(12) United States Patent
Denk et al.

(10) Patent No.: US 12,352,762 B2
(45) Date of Patent: *Jul. 8, 2025

(54) DYNAMIC OF sFlt-1 OR ENDOGLiN/PlGF RATIO AS AN INDICATOR FOR IMMINENT PREECLAMPSIA AND/OR HELLP SYNDROME

(71) Applicant: Roche Diagnostics Operations, Inc., Indianapolis, IN (US)

(72) Inventors: Barbara Denk, Groebenzell (DE); Martin Hund, Horw (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 506 days.

This patent is subject to a terminal disclaimer.

(21) Appl. No.: 17/463,876

(22) Filed: Sep. 1, 2021

(65) Prior Publication Data

US 2022/0128568 A1    Apr. 28, 2022

Related U.S. Application Data

(63) Continuation of application No. 16/373,098, filed on Apr. 2, 2019, now abandoned, which is a continuation of application No. 14/264,377, filed on Apr. 29, 2014, now Pat. No. 10,302,657, which is a continuation of application No. PCT/EP2012/072157, filed on Nov. 8, 2012.

(30) Foreign Application Priority Data

Nov. 9, 2011    (EP) .................................. 11188422

(51) Int. Cl.
G01N 33/68    (2006.01)
C07K 16/22    (2006.01)
G01N 33/74    (2006.01)

(52) U.S. Cl.
CPC ........... *G01N 33/689* (2013.01); *C07K 16/22* (2013.01); *G01N 33/74* (2013.01); *G01N 2333/475* (2013.01); *G01N 2800/368* (2013.01); *G01N 2800/50* (2013.01)

(58) Field of Classification Search
None
See application file for complete search history.

(56) References Cited

U.S. PATENT DOCUMENTS

| 5,744,305 | A | 4/1998 | Fodor et al. |
| 2005/0170444 | A1 | 8/2005 | Karumanchi et al. |
| 2007/0111326 | A1 | 5/2007 | Sogin et al. |
| 2009/0068683 | A1 | 3/2009 | Garovic |

FOREIGN PATENT DOCUMENTS

| EP | 2037278 | A1 | 3/2009 |
| EP | 1804836 | B1 | 11/2010 |
| WO | 2004008946 | A3 | 1/2004 |
| WO | 2006034507 | A3 | 3/2006 |
| WO | 2007059065 | A2 | 5/2007 |
| WO | 2008005814 | A2 | 1/2008 |
| WO | 2011054829 | A1 | 5/2011 |
| WO | 2011067597 | A1 | 6/2011 |

OTHER PUBLICATIONS

Verlohren et al., Am J Obstet Gynecol 2010; 202: 161.e1-11 (Year: 2010).*
Ohkuchi et al., Hypertension Research (2010) 33, 422-427 (Year: 2010).*
Powers et al., PLoS ONE, 2010; 5(10): e13263 (Year: 2010).*
Searle et al., Hypertension, (2011) vol. 58, No. 5, pp. e129-e130. Abstract No. P362; presented at: High Blood Pressure Research 2011 Scientific Sessions, HBPR 2011. Orlando, FL, United States. Sep. 20, 2011-Sep. 24, 2011 (Year: 2011).*
Levine et al., JAMA. 2005; 293: 77-85 (Year: 2005).*
Perkins et al., Cancer Epidemiol Biomarkers Prev 2009;18(10) (Year: 2009).*
Leon Gordis, Chapter 7 in "Epidemiology", Second Edition, Copyright 2000, p. 115 (Year: 2000).*
Levine et al., N Engl J Med 2004; 350: 672-83 (Year: 2004).*
ACOG Practice Bulletin No. 23, Diagnosis and Management of Preeclampsia and Eclampsia Clinical Management Guidelines for Obstetrician-Gynecologists Number 33, Jan. 2002, Obstetrics & Gynecology, Jan. 2002, pp. 159-167, vol. 99, No. 1.
Berg et al., Pregnancy-Relaed Mortality in the United States, 1998 to 2005, Obstetrics & Gynecology, Dec. 2010, pp. 1302-1309, vol. 116, No. 6.
Chen et al., Predictive value of angiogenic factors and uterine artery Doppler for early-versus late-onset pre-eclampsia and intrauterine growth restriction, Ultrasound in Obstetrics & Gynecology, 2008, pp. 303-309, vol. 31.
De Vivo, et al., Endoglin, PlGF and sFlt-1 as markers for predicting pre-eclampsia, Acta Obstetricia et Gynecologica, 2008, pp. 837-842, vol. 87.
Duley, Lelia, The Global Impact of Pre-eclampsia and Eclampsia, Seminars in Perinatology, 2009, pp. 130-137, vol. 33.

(Continued)

*Primary Examiner* — Christina M Borgeest
(74) *Attorney, Agent, or Firm* — Taft Stettinius & Hollister LLP

(57) ABSTRACT

Diagnostic methods and tools relating to diagnosing whether a pregnant subject is at risk for developing preeclampsia and/or early-onset preeclampsia within a short period of time. The methods include determining the amounts of the biomarkers sFlt-1 or Endoglin and PlGF in a first and a second sample of said subject, said first sample being obtained prior to said second sample; calculating a first ratio from the amounts of sFlt-1 or Endoglin and PlGF determined in the first sample, and a second ratio from the amounts of sFlt-1 or Endoglin and PlGF determined in the second sample; and comparing the value of the first and the second ratio, whereby a subject being at risk for developing preeclampsia within a short period of time is diagnosed if the value of the second ratio is increased compared to the value of the first ratio by a factor of at least about 3.

4 Claims, 14 Drawing Sheets

(56) References Cited

OTHER PUBLICATIONS

Kendall, et al., Identification of a Natural Soluble Form of the Vascular Endothelial Growth Factor Receptor, FLT-1 and its Heterodimerization with KDR, Biochemical and Biophysical Research Communications, 1996, pp. 324-328, vol. 226.

Kusanovic, et al., A prospective cohort study of the value of maternal plasma concentrations of angiogenic and anti-angiogenic factors in early pregnancy and mid trimester in the identification of patients destined to develop preeclampsia, The Journal of Maernal-Fetal and Neonatal Medicine, Nov. 2009, pp. 1021-1038, vol. 22, No. 11.

Levine et al., Urinary Placental Growth Factor and Risk of Preeclampsia, Journal of the American Medical Association, 2005, pp. 77-85, vol. 293, No. 1.

Levine et al., Circulating angiogenic factors and the risk of preeclampsia, new England Journal of Medicine, 2004, vol. 350, No. 7, pp. 672-683.

Levine et al., Soluble Endoglin and Other Circulating Antiangiogenic Factors in Preeclampsia, The New England Journal of Medicine, 2006, pp. 992-1005, vol. 355.

Maglione et al., Two alternative mRNAs coding for the angiogenic factor, placenta growth factor (PIGF), are transcribed from a single gene of chromosome 13, Oncogene, 1993, pp. 925-931, vol. 8.

Moore Simas et al., Angiogenic factors for the prediction of preeclampsia in high-risk women, American Journal of Obstetrics & Gynecology, Sep. 2007, pp. 244.e1-244.e8, vol. 197.

Nolan et al., Suspension array technology: evolution of the flat-array paradigm, Trends in Biotechnology, Jan. 2002, pp. 9-12, vol. 20, No. 1.

Ohkuchi et al., Threshold of Soluble Fms-Like Tyrosine Kinase 1/Placental Growth Factor Ration for th elmminent Onset of Preeclampsia, Hypertension, 2011, pp. 859-866, vol. 58.

Ouyang, et al., Plasma sFlt-1-PIGF ratio is correlated with inflammatory but not with oxidative stress in Chinese preeclamptic women, Archives of Gynecology and Obstetrics, 2009, pp. 91-97, vol. 280.

Rana et al., Sequential Changes in Antiagniogenic Factors in Early Pregnancy and Risck of Development Preeclampsia, Hypertension, 2007, pp. 137-142, vol. 50.

Sunderji et al., Automated assays for sVEGF R1 and PIGF as an aid in the diagnosis of preter preeclampsia: a prospective clinical study, American Journal of Obstetrics & Gynecology, Jan. 2010, pp. e1-7, vol. 202, No. 40.

Verlohren et al., Angiogenic growth factors in the diagnosis and prediction of pre-eclampsia, Clinical Science, 2012, pp. 43-52, vol. 122.

Schiettecatte, Multicenter evaluation of the first automated Elecsys sFlt-1 and PIGF assays in normal pregnancies and preeclampsia, Clinical Biochemistry 43, 2010, pp. 768-770.

R & D, Human PIGF Quantikine Elisa kit, 2—pages, retrieved from https://www.rndsystems.com/products/human-plgf-quantikine-elisa-kit_dpg00#dsTAB1 on Jul. 13, 2015.

Gharesi-Fard et al. Proteome Differences of Placenta Between Pre-Eclampsia and Normal Pregnancy, Placenta 31, 2010, pp. 121-125.

Watanbe et al., Proteome ananlysis reveals elevated serum levels of clusterin in patients with preeclampsia, Proteomics, 2004, vol. 4, pp. 537-543.

Bast et al., Translational Crossroads for Biomarkers, Clin Cancer Res, 2005, vol. 11, No. 17, pp. 6103-3408.

Labaer et al., So you want to look for biomarkers, Journal of Proteome Research, 2005, vol. 4, pp. 1053-1059.

Baker et al., Biomarkers We Trust, Nature Biotechnology, 2005, vol. 23, No. 3, pp. 297-304.

Yu Chen, "Novel Angiogenic Factors for Predicting Preeclampsia: sFlt-1, PIGF, and Soluble Endoglin", The Open Clinical Chemistry Journal, vol. 2, pp. 1-6, Published Dec. 31, 2008.

* cited by examiner

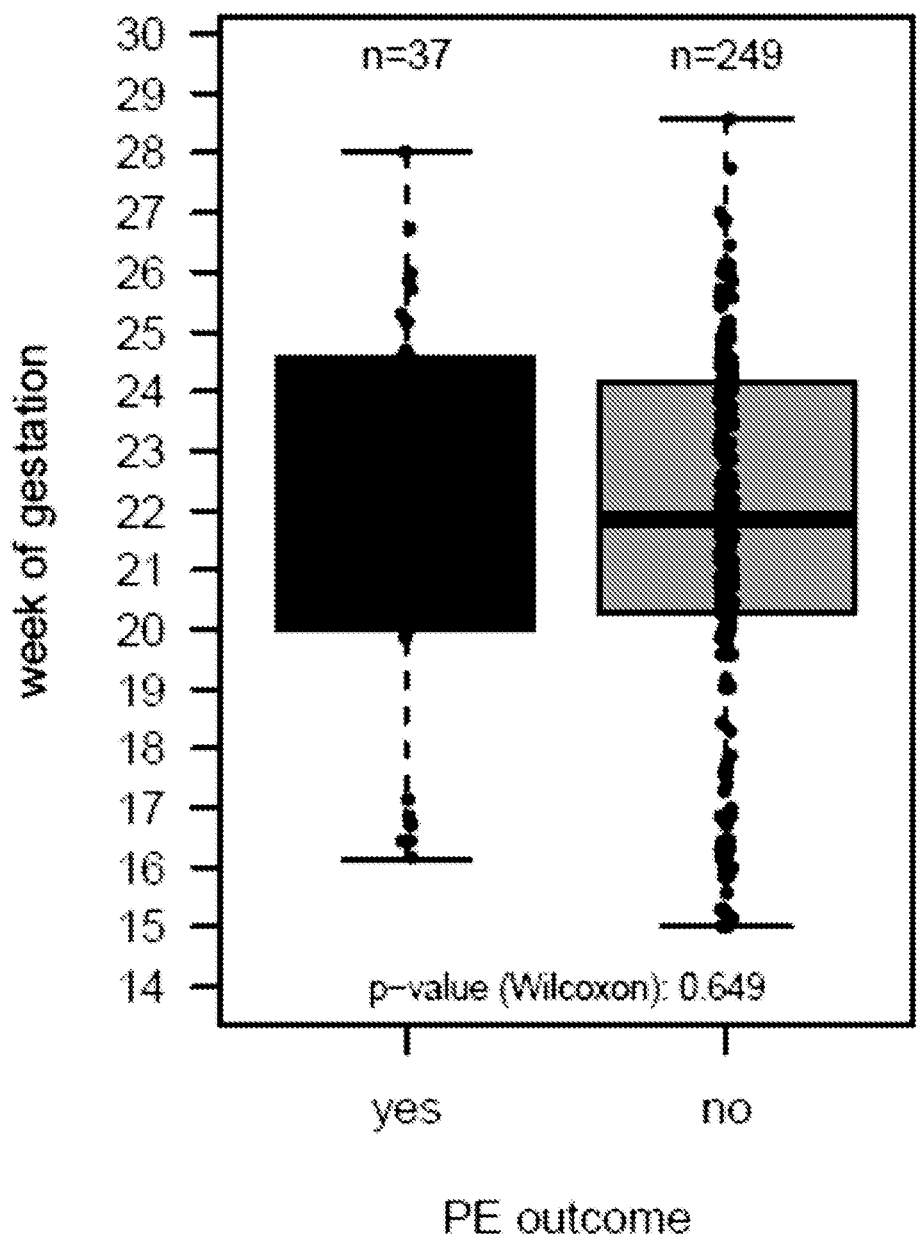
Gestational age at visits and difference

Gestational age at visits and difference sFlt-1/PlGF ratio by visit and PE/HELLP sFlt-1/PlGF ratio by visit and PE/HELLP Differences of sFlt-1/PlGF ratio vs. gestational age / point of measurement left: Time to diagnosis of PE/HELLP vs. both values of sFlt-1/PlGF ratio; right: Slopes only from patients with date of PE/HELLP diagnosis available left: Time to diagnosis of PE/HELLP vs. both values of sFlt-1/PlGF ratio; right: Slopes only from patients with date of PE/HELLP diagnosis available

DYNAMIC OF sFlt-1 OR ENDOGLiN/PlGF RATIO AS AN INDICATOR FOR IMMINENT PREECLAMPSIA AND/OR HELLP SYNDROME

CROSS-REFERENCE TO RELATED APPLICATIONS

This application is a continuation application of U.S. patent application Ser. No. 16/373,098, filed Apr. 2, 2019, which is a continuation application of U.S. patent application Ser. No. 14/264,377, filed Apr. 29, 2014 (patented as U.S. Pat. No. 10,302,657, issued May 28, 2019), which is a continuation of International Application No. PCT/EP2012/072157, filed Nov. 8, 2012, which claims the benefit of European Patent Application No. 11188422.7, filed Nov. 9, 2011, the disclosures of which are hereby incorporated by reference in their entirety.

BACKGROUND OF THE DISCLOSURE

Pregnancy may be complicated in different ways, it is on one hand associated with pregnancy related mortality of the pregnant woman and, on the other hand, also associated with increased morbidity and mortality of the newborn. Maternal mortality at a rate of 14.5 per 100,000 live births, is more frequent in pregnant women above the age of 39 years and may be caused by haemorrhage, thrombotic pulmonary embolism, infections, cardiomyopathy and cardiovascular and noncardiovascular conditions as well as hypertensive disorders among which preeclampsia is frequent (Berg 2010, Obstretics and Gynecology: 116: 1302-1309).

Preeclampsia complicates approximately 2 to 8 percent of all pregnancies and is a major contributor to maternal and fetal mortality worldwide (Duley 2009, Semin Perinatol: 33: 130-37). Preeclampsia is generally defined as pregnancy associated or induced hypertension. It is characterized by hypertension and proteinuria. Hypertension is defined in this context as blood pressure of 140 mmHg (systolic) to 90 mmHg (diastolic) or more at two independent measurements, wherein said two measurements have been made at least 6 hours apart. Proteinuria is indicated by 300 mg/dL protein or more in a 24-hour urine sample. However, the definitions of preeclampsia are subject to debate and can differ among societies.

SUMMARY OF THE DISCLOSURE

The instant disclosure provides a reliable assay for identifying apparently healthy pregnant females that are at risk of developing imminent preeclampsia and, in particular, imminent early-onset-preeclampsia Embodiments of the invention are concerned with diagnostic methods and tools. Specifically, the present invention relates to a method for diagnosing whether a pregnant subject is at risk for developing preeclampsia within a short period of time comprising: (a) determining the amounts of the biomarkers sFlt-1 or Endoglin and PlGF in a first and a second sample of said subject, wherein said first sample has been obtained prior to said second sample, (b) calculating a first ratio from said amounts of sFlt-1 or Endoglin and PlGF determined in the first sample and a second ratio from said amounts of sFlt-1 or Endoglin and PlGF determined in the second sample and (c) comparing the value of the said first and the said second ratio, whereby a subject being at risk for developing preeclampsia within a short period of time is diagnosed if the value of the second ratio is increased compared to the value of the first ratio by a factor of at least about 3. The present invention further relates to a method for differentiating between a pregnant subject being at risk of developing early-onset-preeclampsia and a pregnant subject being not at risk of developing early-onset-preeclampsia. Moreover, encompassed by the invention are devices and kits for carrying out these methods. The present invention also relates to a system for performing an optimized risk assessment of developing preeclampsia as disclosed herein and to reagents and kits used in performing the methods disclosed herein.

BRIEF DESCRIPTION OF THE DRAWINGS

The features of this disclosure, and the manner of attaining them, will become more apparent and the disclosure itself will be better understood by reference to the following description of embodiments of the disclosure taken in conjunction with the accompanying drawing.

FIG. 1A shows a graph presenting the distribution of the week of gestation for individual subjects in the study for the group of preeclampsia (PE) outcome patients and the healthy controls. The first visit is shown in the box plots.

Figure 1B:
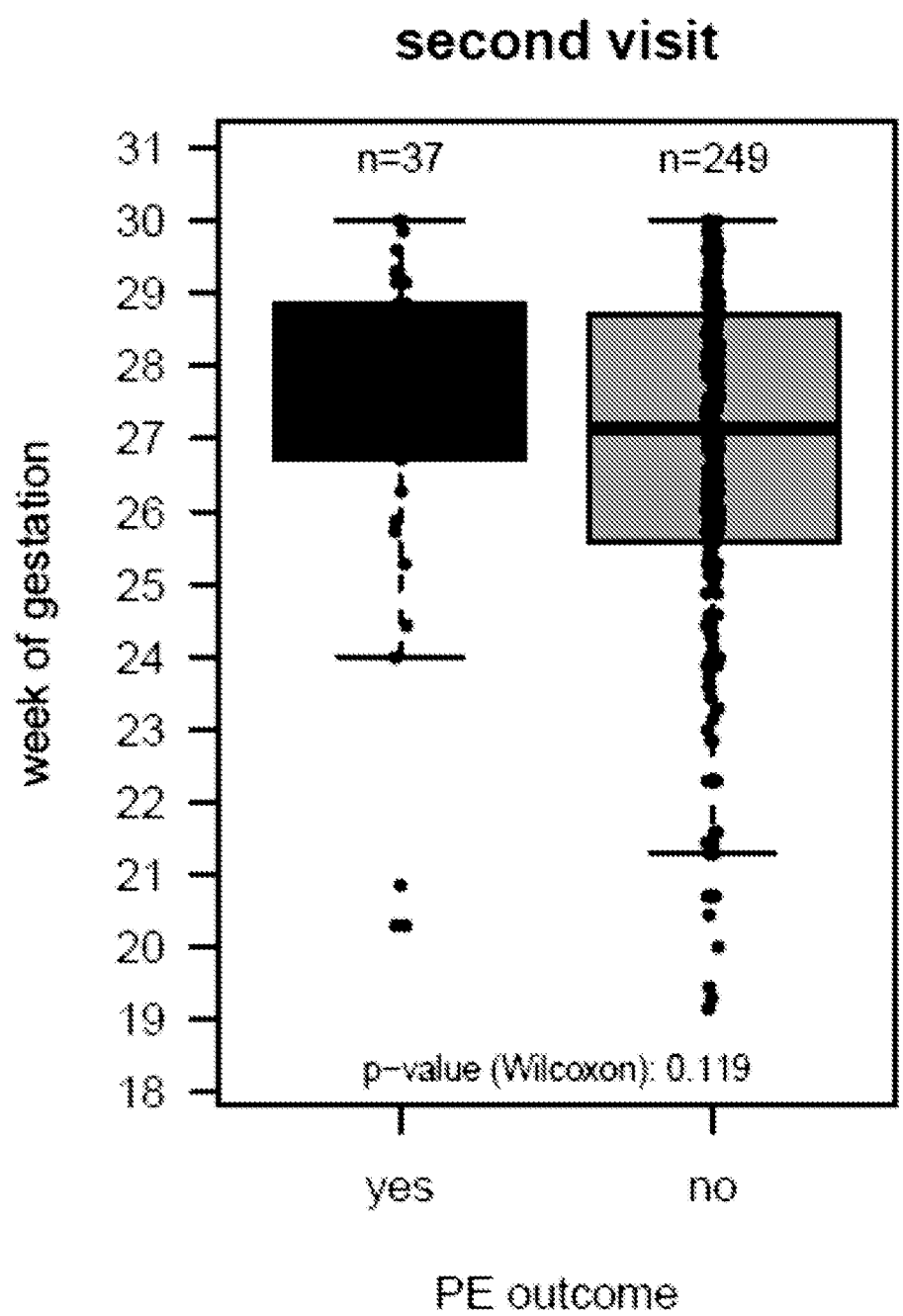
FIG. 1B shows another graph presenting the distribution of the week of gestation for individual subjects in the study for the group of preeclampsia (PE) outcome patients and the healthy controls. The second visit is shown in the box plots.
Figure 1C:
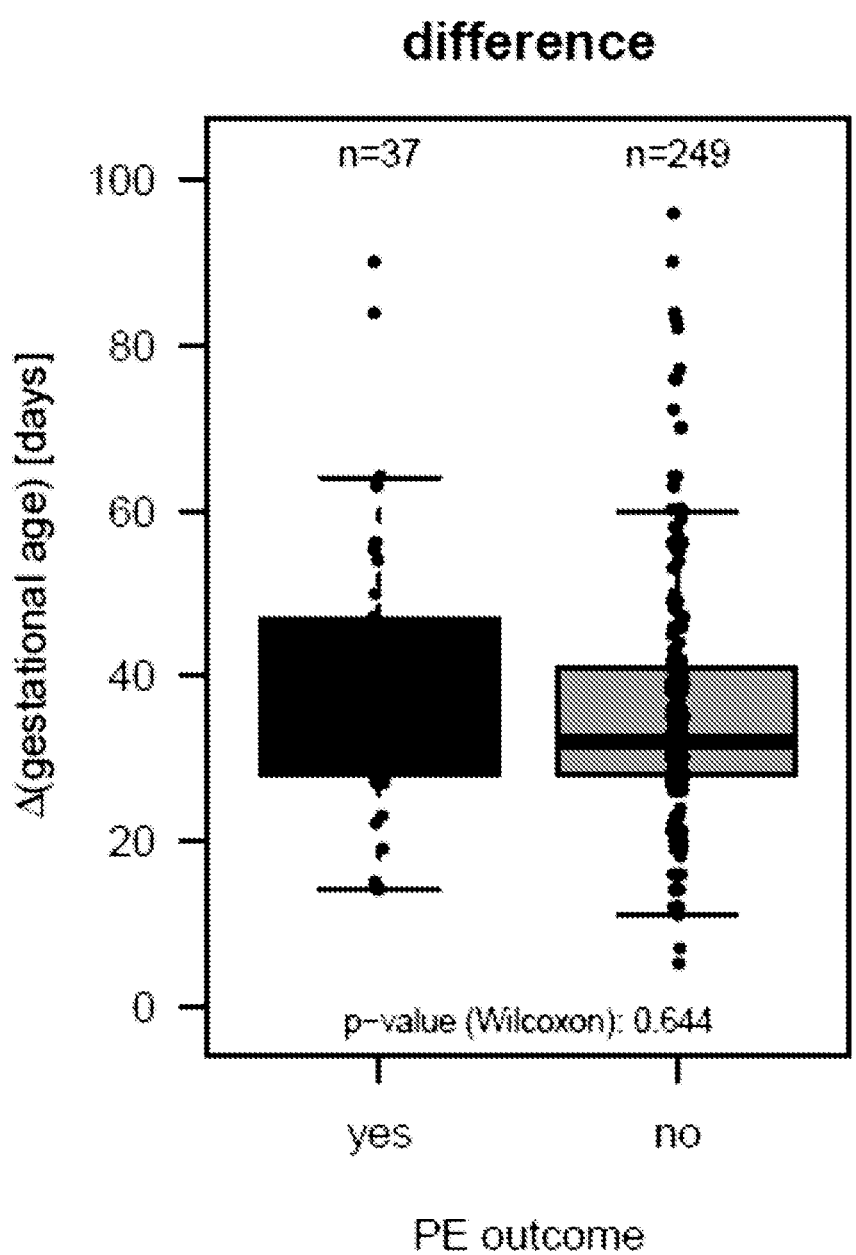
FIG. 1C shows a graph presenting the distribution of the week of gestation for individual subjects in the study for the group of preeclampsia (PE) outcome patients and the healthy controls. The time difference in days between the visits is shown in the box plots.
Figure 2A:
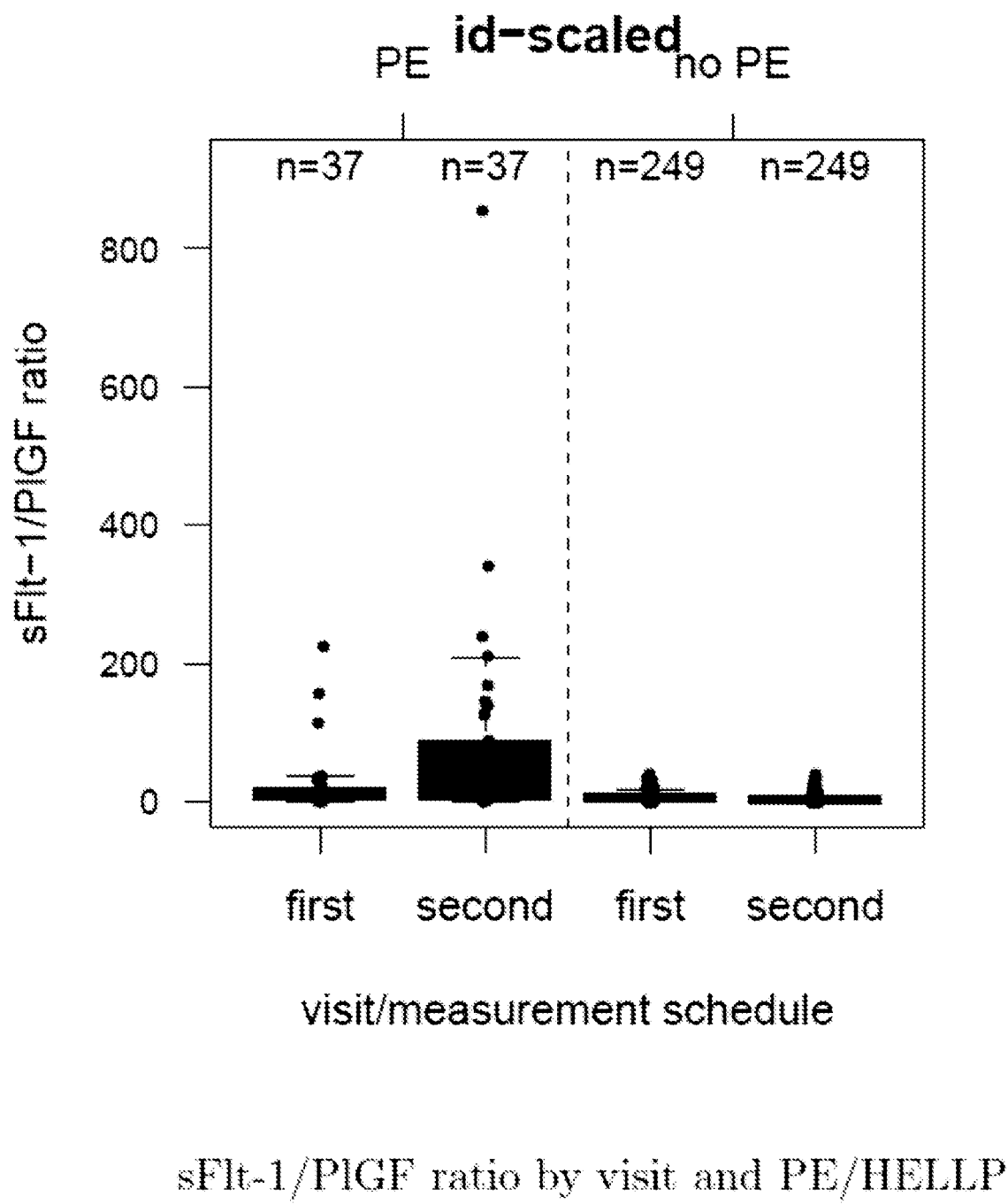
FIG. 2A shows sFlt-1/PlGF ratios for the PE group and the healthy controls at different visits in normal and log scales.
Figure 2B:
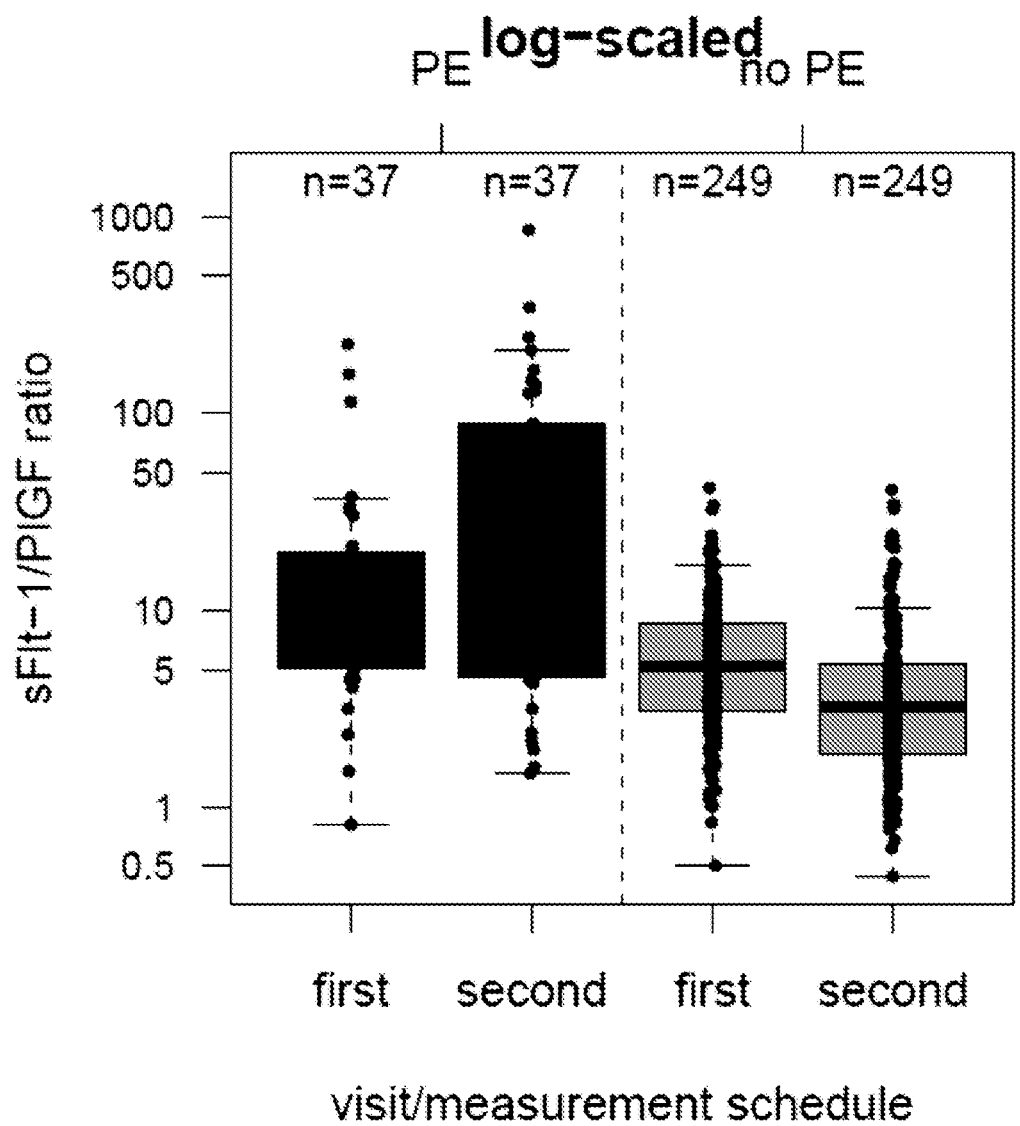
FIG. 2B shows another graph presenting sFlt-1/PlGF ratios for the PE group and the healthy controls at different visits in normal and log scales.
Figure 3A:
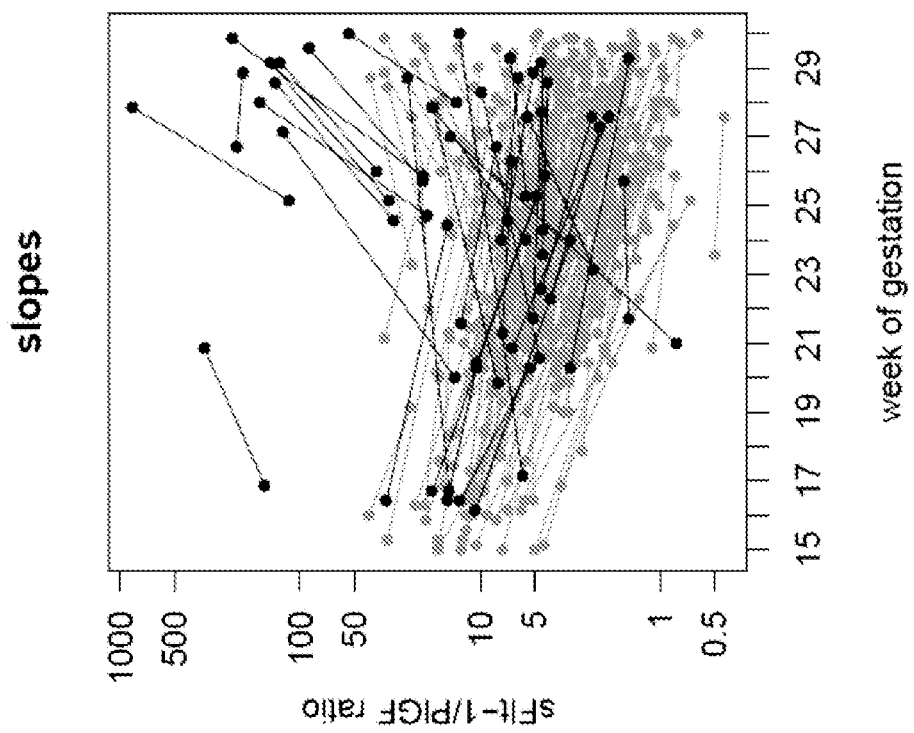
FIG. 3A shows differences of sFlt-1/PlGF ratios compared to gestational age.
Figure 3B:
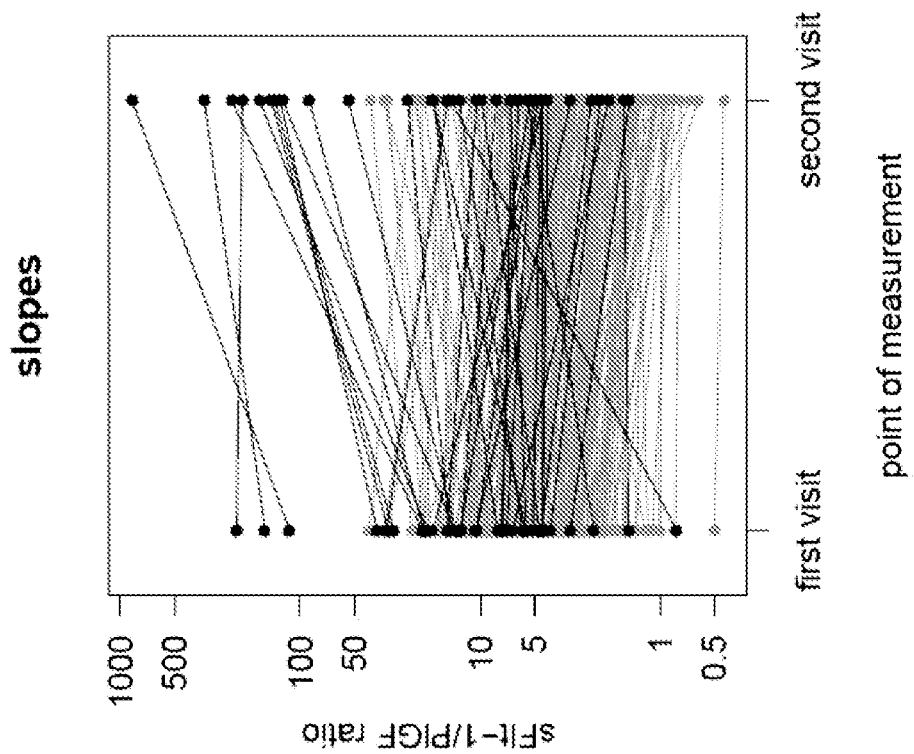
FIG. 3B presents another graph showing differences of sFlt-1/PlGF ratios compared to the time point of measurement.
Figure 4A:
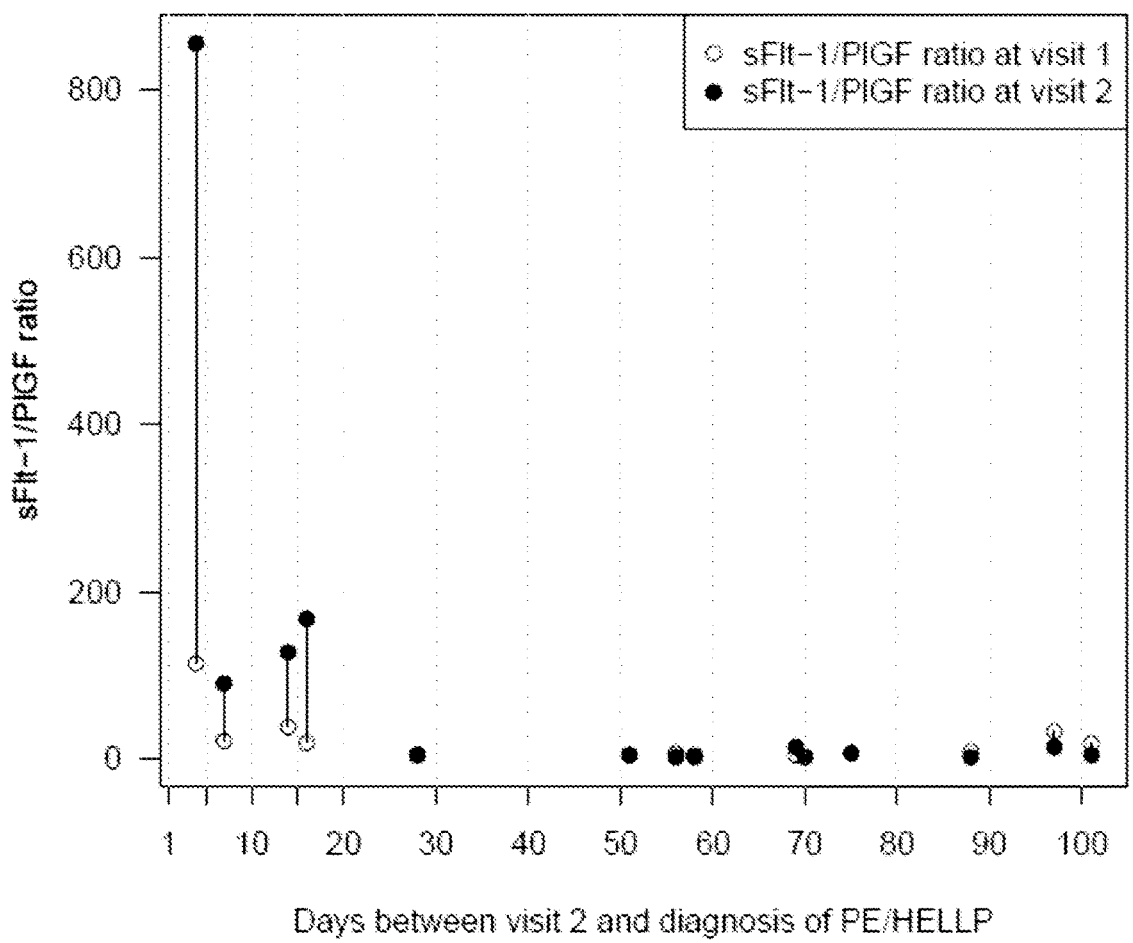
FIG. 4A shows a time to diagnosis of PE/HELLP versus both values of sFlt-1/PlGF ratio plot (left).
Figure 4B:
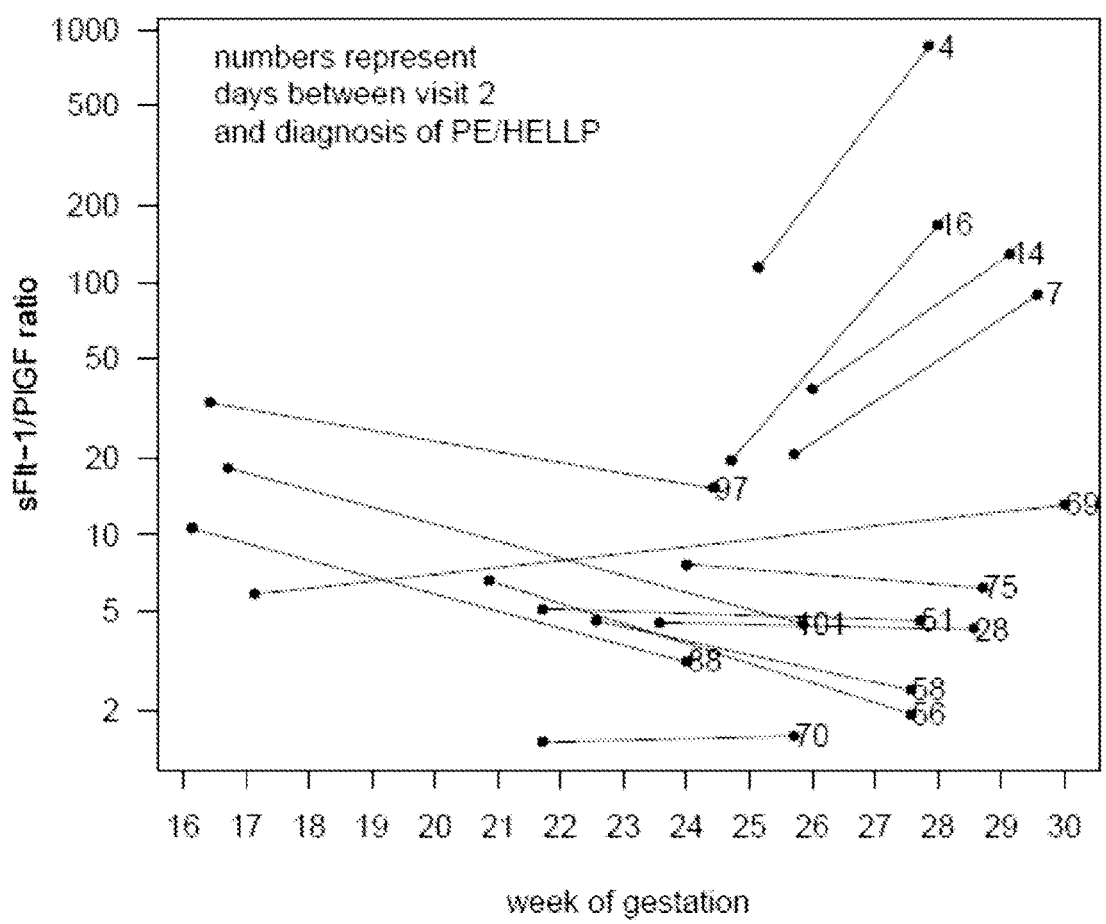
FIG. 4B shows the slopes between the sFlt-1/PlGF ratios at first and second visit from patients of the PE/HELLP group.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

DETAILED DESCRIPTION OF THE EMBODIMENTS OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

Preeclampsia complicates approximately 2 to 8 percent of all pregnancies and is a major contributor to maternal and fetal mortality worldwide (Duley 2009, Semin Perinatol: 33: 130-37). Preeclampsia is generally defined as pregnancy associated or induced hypertension. It is characterized by hypertension and proteinuria. Hypertension is defined in this context as blood pressure of 140 mmHg (systolic) to 90 mmHg (diastolic) or more at two independent measurements, wherein said two measurements have been made at least 6 hours apart. Proteinuria is indicated by 300 mg/dL protein or more in a 24-hour urine sample. However, the definitions of preeclampsia are subject to debate and can differ among societies. Details are also found in the standard text books of medicine and the Guidelines of the various clinical societies, e.g., ACOG Practice Bulletin, Clinical Management Guidelines for Obstetrician—Gynecologists, no.: 33, January 2002 or Leitlinien, Empfehlungen, Stellungnahmen of the Deutschen Gesellschaft fOr Gynakologie and Geburtshilfe e.V., August 2008.

The pathogenesis of preeclampsia is largely unknown. It is believed, however, to be caused by disturbed placental function associated with impaired remodeling of the spiral artery. Flow defects occurring in the process of the development of preeclampsia are associated with ischemia that ultimately results in the release of anti-angiogenic factors into the circulations such as sFlt-1 and Endoglin.

The sole treatment of preeclampsia until today is the termination of pregnancy either by premature vaginal or caesarean delivery. As discussed above maternal risks and fetal viability are significantly impaired in case of preeclampsia before gestational week 34. Accordingly, attempts should be made to delay delivery and to thereby improve survival of the newborn.

The early and reliable diagnosis of preeclampsia and, in particular, the early onset type of preeclampsia which occurs as early as 20 to 34 weeks of gestation is decisive for clinical management of the disease. It will be understood that pregnant females suffering from preeclampsia need special care such as close monitoring, supportive therapeutic measures and, in the case of progression into severe preeclampsia, hospitalization in specialized hospitals having maternal fetal intensive care units (MFICUs). In particular, the early-onset-preeclampsia is challenging for the clinicians in light of the severe side-effects and the usual adverse outcomes associated therewith. Moreover, the early and reliable diagnosis of preeclampsia as well as the prediction of preeclampsia is decisive for the planning of preventive or therapeutic intervention studies (Ohkuchi 2011, Hypertension 58: 859-866).

Accordingly, embodiments of the present invention relate to a method for diagnosing whether a pregnant subject is at risk for developing preeclampsia within a short period of time comprising: a) determining the amounts of the biomarkers sFlt-1 or Endoglin and PlGF in a first and a second sample of said subject, wherein said first sample has been obtained prior to said second sample; b) calculating a first ratio from said amounts of sFlt-1 or Endoglin and PlGF determined in the first sample and a second ratio from said amounts of sFlt-1 or Endoglin and PlGF determined in the second sample; c) comparing the value of the said first and the said second ratio, whereby a subject being at risk for developing preeclampsia within a short period of time is diagnosed if the value of the second ratio is increased compared to the value of the first ratio by a factor of at least about 3.

The method of the present invention may comprise an ex vivo method. Moreover, it may comprise steps in addition to those explicitly mentioned above. For example, further steps may relate to sample pre-treatments or evaluation of the results obtained by the method. The method may be carried out manually or assisted by automation. For example, step (a), (b) and/or (c) may in total or in part be assisted by automation, e.g., by a suitable robotic and sensory equipment for the determination in step (a), a computer-implemented calculation algorithm on a data processing device in step (b) or comparison and/or diagnosis algorithm on a data processing device in step (c).

Accordingly, the present invention also relates to a system for optimizing a risk assessment based on a clinical prediction rule for classifying pregnant subjects, comprising a) an analyzer unit configured to contact, in vitro, a portion of a second sample from a pregnant subject with a ligand comprising specific binding affinity for sFlt-1 and/or Endoglin and configured to contact, in vitro, a portion of a sample from a pregnant subject with a ligand comprising specific binding affinity for PlGF; b) an analyzer unit configured to detect a signal from the portions of the sample from the subject contacted with the ligands, c) a computing device having a processor and in operable communication with said analysis units, and d) a non-transient machine readable media including a plurality of instruction executable by a processor, the instructions, when executed, calculating an amount of sFlt-1 and/or Endoglin, calculating an amount of PlGF, calculating a second ratio from said amounts of sFlt-1 or Endoglin and PlGF determined in the sample and comparing the ratio thus calculated with a first ratio obtained from a first sample, thereby optimizing the risk assessment based on the clinical prediction rule for classifying pregnant subjects.

The term "preeclampsia" as used herein refers to a medical condition which is characterized by hypertension and proteinuria. Preeclampsia occurs in pregnant female subjects and the hypertension is also referred to as pregnancy-induced hypertension. The pregnancy-induced hypertension may be identified to be present in a subject by two blood pressure measurements of 140 mmHg (systolic) to 90 mmHg (diastolic) or more, wherein said two measurements have been made at least 6 hours apart. Proteinuria may be identified to be present by 300 mg/dL protein or more in a 24-hour urine sample. Preeclampsia may progress to eclampsia, a life-threatening disorder characterized by the appearance of tonic-clonic seizures or coma conditions. Symptoms associated with severe preeclampsia are oligouria of less than 500 ml within 24 hours, cerebral or visual disturbance, pulmonary edema or cyanosis, epigastric- or right upper quadrant- pain, impaired liver function, thrombocytopenia, fetal growth restriction. Subjects suffering from preeclampsia with hepatic involvement may further develop the HELLP syndrome. Accordingly, a subject according to the invention which is at risk of developing preeclampsia, may also potentially be at risk of developing the HELLP syndrome. The HELLP syndrome is associated with a high risk of adverse outcomes such as placental abruption, renal failure, subcapsular hepatic hematoma, recurrent preeclampsia, preterm delivery, or even materal and/or fetal death. Further details of preeclampsia and the accompanying symptoms as well as the follow up diseases such as HELLP syndrome or eclampsia can be found, for example, in standard text books of medicine or Guidelines of the relevant medical societies. Details can be found, e.g., in ACOG Practice Bulletin, Clinical Management Guidelines for Obstetrician—Gynecologists, no.: 33, January 2002 or Leitlinien, Empfehlungen, Stellungnahmen of the Deutschen Gesellschaft fOr Gynakologie and Geburtshilfe e.V., August 2008. Preeclampsia occurs in up to 10% of pregnancies usually in the second or third trimester. However, some females develop preeclampsia as early as in week 20 of gestation.

Within week 20 to 34 of gestation, preeclampsia is also called early-onset-preeclampsia while preeclampsia which occurs after week 34 of gestation is also termed late-onset-preeclampsia. It will be understood that the early-onset-preeclampsia, usually, is accompanied by more severe side-effects and adverse outcomes compared to the usually relatively mild late-onset-preeclampsia. The phrase "at risk for developing preeclampsia" refers to a pregnant subject which will develop preeclampsia within a prognostic time window in the future with a statistically significantly increased likelihood compared to a pregnant subject which is not at risk for developing preeclampsia. For example, that likelihood may be at least 80%, at least 85%, at least 90%, at least 95%, at least 97%, at least 98%, at least 99% or up to 100%. Further details on statistics are found elsewhere herein.

The term "subject" as used herein relates to animals, for example mammals, and humans. The subject according to the present invention is a pregnant subject, i.e. a pregnant female. According to various embodiments, the subject according to the present invention exhibits no symptoms of preeclampsia. Such symptoms of preeclampsia include clinical symptoms of preeclampsia as specified elsewhere herein. The symptoms may comprise at least one symptom selected from the group consisting of: epigastric pain, headache, visual disturbance, and edema. However, the subject according to the present invention may also exhibit at least one of the aforementioned symptoms and may, thus, be suspected to suffer from preeclampsia already.

In some embodiments, the pregnant subject according to the present invention is between about week 15 and about week 34 of gestation, for example between about week 15 and about week 30 of gestation.

According to instant disclosure, the method of the present invention can be used in routine screening approaches of apparently healthy pregnant subjects. However, the pregnant subject envisaged by the present invention may also belong into a risk group having a higher prevalence for preeclampsia. Pregnant subjects suffering from adiposity, hypertension, autoimmune diseases such as Lupus erythematosus, thrombophilias or diabetes mellitus have an increased prevalence for developing preeclampsia in general. The same applies for subjects that suffered from preeclampsia, eclampsia and/or HELLP syndrome in a previous pregnancy. Furthermore, elderly females who are pregnant for the first time do also exhibit a predisposition for developing preeclampsia. The likelihood for developing preeclampsia, however, is decreasing with the number of pregnancies.

The term "diagnosing" as used herein means assessing whether a subject is at risk of developing preeclampsia within a short period of time, or not. In some embodiments, said short period of time is a period of time less than 4 weeks, or between about 2 to about 3 weeks, and, in some cases, a time period of about 16 days. As will be understood by those skilled in the art, such an assessment is usually not intended to be correct for 100% of the subjects to be diagnosed. The term, however, requires that the assessment is correct for a statistically significant portion of the subjects (e.g., a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found, for example, in Dowdy and Wearden, Statistics for Research, John Wiley & Sons, New York 1983. Exemplary conditions of confidence intervals according to the instant disclosure are at least 90%, at least 95%, at least 97%, at least 98% or at least 99%. The p-values are, preferably, 0.1, 0.05, 0.01, 0.005, or 0.0001.

The term "sample" refers to a sample of a body fluid, to a sample of separated cells or to a sample from a tissue or an organ. Samples of body fluids can be obtained by well-known techniques and include, samples of blood, plasma, serum, or urine. Tissue or organ samples may be obtained from any tissue or organ by, e.g., biopsy. Separated cells may be obtained from the body fluids or the tissues or organs by separating techniques such as centrifugation or cell sorting. Cell-, tissue- or organ samples are obtained from those cells, tissues or organs which express or produce the peptides referred to herein.

The "first sample" according to the method of the present invention has been obtained prior to the "second sample". It will be understood that the first sample and the second sample are samples of the same type of sample material, i.e., are from the same type of body fluid, cells, tissue or organ. Moreover, the first sample has been prior to the second sample, for example, at two subsequent regular medical investigations during pregnancy wherein the first sample has been taken at the earlier investigation and the second sample has been taken at the later investigation.

According to some embodiments, the first sample has been obtained about 1 week to about 15 weeks, about 2 weeks to about 6 weeks and, in some cases about 4 to about 5 weeks prior to the said second sample.

The term "sFlt-1" as used herein refers to polypeptide which is a soluble form of the fms-like tyrosine kinase 1. The polypeptide is also referred to as soluble VEGF receptor 1 (sVEGF R1) in the art (see, e.g., Sunderji 2010, Am J Obstet Gynecol 202: 40e1-7). It was identified in conditioned culture medium of human umbilical vein endothelial cells. The endogenous sFlt1 receptor is chromatographically and immunologically similar to recombinant human sFlt1 and binds [125I] VEGF with a comparable high affinity. Human sFlt1 is shown to form a VEGF-stabilized complex with the extracellular domain of KDR/Flk-1 in vitro. According to the instant disclosure, sFlt1 refers to human sFlt1 as describe in Kendall 1996, Biochem Biophs Res Commun 226(2): 324-328; for amino acid sequences, see, e.g., also Genebank accession numbers P17948, Cl: 125361 for human and BAA24499.1, Cl: 2809071 for mouse sFlt-1 (Genebank is available from the NCBI, USA under ncbi.nlm.nih.gov/entrez). The term also encompasses variants of the aforementioned human sFlt-1 polypeptides. Such variants have at least the same essential biological and immunological properties as the aforementioned sFlt-1 polypeptide. In particular, they share the same essential biological and immunological properties if they are detectable by the same specific assays referred to in this specification, e.g., by ELISA assays using polyclonal or monoclonal antibodies specifically recognizing the said sFlt-1 polypeptides. Moreover, it is to be understood that a variant as referred to in accordance with the present invention shall have an amino acid sequence which differs due to at least one amino acid substitution, deletion and/or addition wherein the amino acid sequence of the variant is still, for example, at least 50%, 60%, 70%, 80%, 85%, 90%, 92%, 95%, 97%, 98%, or 99% identical with the amino sequence of the specific sFlt-1 polypeptide, in some cases over the entire length of the human sFlt-1, respectively. The degree of identity between two amino acid sequences can be determined by algorithms well known in the art. According to some embodiments, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm disclosed by Smith 1981, Add. APL. Math. 2:482, by the homology alignment algorithm of Needleman 1970, J. Mol. Biol. 48:443, by the search for similarity method of Pearson 1988, Proc. Natl. Acad Sci. (USA) 85: 2444, by computerized implementations of these algorithms (GAP, BESTFIT, BLAST, FAST, PASTA, and TFASTA in the Wisconsin Genetics Software Package, Genetics Computer Group (GCG), 575 Science Dr., Madison, WI), or by visual inspection. Given that two sequences have been identified for comparison, GAP and BESTFIT are employed to determine their optimal alignment and, thus, the degree of identity. According to some embodiments, the default values of 5.00 for gap weight and 0.30 for gap weight length are used. Variants referred to above may be allelic variants or any other species specific homologs, paralogs, or orthologs. Variants referred to above may be allelic variants or any other species specific homologs, paralogs, or orthologs. Moreover, the variants referred to herein include fragments or subunits of the specific sFlt-1 polypeptides or the aforementioned types of variants as long as these fragments have the essential immunological and biological properties as referred to above. Such fragments may be, e.g., degradation products of the sFlt-1 polypeptides. Variants are deemed to share the same essential biological and immunological properties if they are detectable by the same specific assays referred to in this specification, e.g., by ELISA assays using polyclonal or monoclonal antibodies specifically recognizing the said sFlt-1 polypeptides. An illustrative assay is described in the accompanying Examples. Further included are variants which differ due to posttranslational modifications such as phosphorylation or myristylation. sFlt-1 may be detected in bound or free form or as total sFlt-1 amount in a sample.

The term "Endoglin" as used herein refers to a polypeptide having a molecular weight of 180 kDa non-reduced, 95 kDa after reduction and 66 kDa in its reduced and N-deglycosylated form. The polypeptide is capable of forming dimers and binds to TGF-13 and TGF-13 receptors. Also, Endoglin refers to human Endoglin. According to embodiments of the instant disclosure, human Endoglin has an amino acid sequence as shown in Genebank accession number AAC63386.1, GI: 3201489. Two Endoglin isoforms, S-Endoglin and L-Endoglin have been described. L-Endoglin consists of total of 633 amino acids with a cytoplasmic tail of 47 amino acids while S-Endoglin consists of 600 amino acids with a cytoplasmic tail of 14 amino acids. According to some embodiments, Endoglin as used herein is soluble Endoglin (sEng). Soluble Endoglin as referred to herein is preferably described in EP 1 804 836 B 1. Moreover, it is to be understood that a variant as referred to in accordance with the present invention may have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific Endoglin. Variants may be allelic variants, splice variants or any other species specific homologs, paralogs, or orthologs. Moreover, the variants referred to herein include fragments of the specific Endoglin or the aforementioned types of variants as long as these fragments have the essential immunological and biological properties as referred to above. Such fragments may be, e.g., degradation products of Endoglin. Variants are deemed to share the same essential biological and immunological properties if they are detectable by the same specific assays referred to in this specification, e.g., by ELISA assays using polyclonal or monoclonal antibodies specifically recognizing the said Endoglin polypeptides. An exemplary assay is described in the accompanying Examples. Further included are variants which differ due to posttranslational modifications such as phosphorylation or myristylation. Endoglin may be detected in bound or free form or as total Endoglin amount in a sample.

The term "PlGF (Placental Growth Factor)" as used herein refers to a placenta derived growth factor which is a polypeptide having 149 amino acids in length and being highly homologous to the platelet-derived growth factor-like region of human vascular endothelial growth factor (VEGF). Like VEGF, PlGF has angiogenic activity in vitro and in vivo. For example, biochemical and functional characterization of PlGF derived from transfected COS-1 cells revealed that it is a glycosylated dimeric secreted protein which is able to stimulate endothelial cell growth in vitro (Maqlione 1993, Oncogene 8(4):925-31). According to embodiments of the instant disclosure, PlGF refers to human PlGF, for example, to human PlGF having an amino acid sequence as shown in Genebank accession number P49763, GI: 17380553. The term encompasses variants of said specific human PlGF. Such variants have at least the same essential biological and immunological properties as the specific PlGF polypeptide. Variants are deemed to share the same essential biological and immunological properties if they are detectable by the same specific assays referred to in this specification, e.g., by ELISA assays using polyclonal or monoclonal antibodies specifically recognizing the said PlGF polypeptides. An exemplary assay is described in the accompanying Examples. Moreover, it is to be understood that a variant as referred to in accordance with the present invention shall have an amino acid sequence which differs due to at least one amino acid substitution, deletion and/or addition wherein the amino acid sequence of the variant is still, for example, at least 50%, 60%, 70%, 80%, 85%, 90%, 92%, 95%, 97%, 98%, or 99% identical with the amino sequence of the specific PlGF polypeptides. The degree of identity between two amino acid sequences can be determined by algorithms well known in the art and described elsewhere herein. Variants referred to above may be allelic variants or any other species specific homologs, paralogs, or orthologs. Moreover, the variants referred to herein include fragments of the specific PLGF polypeptides or the aforementioned types of variants as long as these fragments have the essential immunological and biological properties as referred to above. Such fragments may be, e.g., degradation products or splice variants of the PLGF polypeptides. Further included are variants which differ due to posttranslational modifications such as phosphorylation or myristylation. PlGF may be detected in bound or free form or as total PlGF amount in a sample.

Determining the amount of any peptide or polypeptide referred to in this specification relates to measuring the amount or concentration, for example, semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e., a component not being the peptide or polypeptide itself) or a biological read out system, e.g., measurable cellular responses, ligands, labels, or enzymatic reaction products.

In accordance with the present invention, determining the amount of a peptide or polypeptide can be achieved by all known means for determining the amount of a peptide in a sample. Said means comprise immunoassay devices and methods which may utilize labeled molecules in various sandwich, competition, or other assay formats. Said assays will develop a signal which is indicative for the presence or absence of the peptide or polypeptide. Moreover, the signal strength can, for example, be correlated directly or indirectly (e.g. reverse- proportional) to the amount of polypeptide present in a sample. Further suitable methods comprise measuring a physical or chemical property specific for the peptide or polypeptide such as its precise molecular mass or NMR spectrum. Said methods comprise, in some example embodiments, biosensors, optical devices coupled to immunoassays, biochips, analytical devices such as mass-spectrometers, NMR-analysers, or chromatography devices. Further, methods include micro-plate ELISA-based methods, fully-automated or robotic immunoassays (available for example on ELECSYS™ analyzers), CBA (an enzymatic Cobalt Binding Assay, available, for example, on ROCHE-HITACHI™ analyzers), and latex agglutination assays (available, for example, on ROCHE-HITACHI™ analyzers).

According to embodiments of the instant disclosure, determining the amount of a peptide or polypeptide comprises the steps of (a) contacting a cell capable of eliciting a cellular response the intensity of which is indicative of the amount of the peptide or polypeptide with the said peptide or polypeptide for an adequate period of time, (b) measuring the cellular response. For measuring cellular responses, the sample or processed sample is, for example, added to a cell culture and an internal or external cellular response is measured. The cellular response may include the measurable expression of a reporter gene or the secretion of a substance, e.g., a peptide, polypeptide, or a small molecule. The expression or substance shall generate an intensity signal which correlates to the amount of the peptide or polypeptide. According to a illustrative embodiments, said steps of contacting, removing and measuring may be performed by an analyser unit of the system disclosed herein. According to some embodiments, said steps may be performed by a single analyzer unit of said system or by more than one analyser unit in operable communication with each other. For example, according to a specific embodiment, said system disclosed herein may include a first analyser unit for performing said steps of contacting and removing and a second analyser unit, operably connected to said first analyzer unit by a transport unit (for example, a robotic arm), which performs said step of measuring.

Also, according to embodiments of the instant disclosure, determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may, for example, comprise the steps of (a) contacting the peptide with a specific ligand, (b) removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide described herein. Exemplary ligands include antibodies, nucleic acids, peptides or polypeptides such as receptors or binding partners for the peptide or polypeptide and fragments thereof comprising the binding domains for the peptides, and aptamers, e.g., nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g., phage display. Antibodies as referred to herein include both polyclonal and monoclonal antibodies, as well as fragments thereof, such as Fv, Fab and F(ab)2 fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. According to embodiments of the instant disclosure, the ligand or agent binds specifically to the peptide or polypeptide. Specific binding according to the present invention means that the ligand or agent should not bind substantially to, i.e., cross-react with, another peptide, polypeptide or substance present in the sample to be analyzed. According to embodiments of the instant disclosure, the specifically bound peptide or polypeptide should be bound with at least 3 times higher, more for example, at least 10 times higher and even more for example at least 50 times higher affinity than any other relevant peptide or polypeptide. Non-specific binding may be tolerable, if it can still be distinguished and measured unequivocally, e.g., according to its size on a Western Blot, or by its relatively higher abundance in the sample. Binding of the ligand can be measured by any method known in the art. According to embodiments of the instant disclosure, said method is semi-quantitative or quantitative. Further suitable techniques for the determination of a polypeptide or peptide are described in the following.

Also, binding of a ligand may be measured directly, e.g., by NMR or surface plasmon resonance. Measurement of the binding of a ligand, according to some embodiments, is performed by an analyzer unit of a system disclosed herein. Thereafter, an amount of the measured binding may be calculated by a computing device of a system disclosed herein. Second, if the ligand also serves as a substrate of an enzymatic activity of the peptide or polypeptide of interest, an enzymatic reaction product may be measured (e.g. the amount of a protease can be measured by measuring the amount of cleaved substrate, e.g., on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, in some illustrative cases the amount of substrate is saturating. The substrate may also be labeled with a detectable label prior to the reaction. According to embodiments of the instant disclosure, the sample is contacted with the substrate for an adequate period of time. An adequate period of time refers to the time necessary for a detectable, in some cases, amount of product to be produced. Instead of measuring the amount of product, the time necessary for appearance of a given (e.g., detectable) amount of product can be measured. Also, the ligand may be coupled covalently or non-covalently to a label allowing detection and measurement of the ligand.

Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.).

The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag may be at the N-terminus and/or C-terminus.

Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-aminobenzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences).

A suitable enzyme-substrate combination may result in a colored reaction product, fluorescence or chemoluminescence, which can be measured according to methods known in the art (e.g. using a light-sensitive film or a suitable camera system). As for measuring the enyzmatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include $^{35}$S, $^{125}$I, $^{32}$V, $^{33}$P and the like. A radioactive label can be detected by any method known and appropriate, e.g. a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamide gel electrophoresis (SDS-PAGE), Western Blotting, and mass spectrometry), can be used alone or in combination with labeling or other detection methods as described above.

The amount of a peptide or polypeptide may be, for example, determined as follows: (a) contacting a solid support comprising a ligand for the peptide or polypeptide as specified above with a sample comprising the peptide or polypeptide, (b) removing unbound peptide or polypeptide as well as remaining sample material and (c) measuring the amount peptide or polypeptide which is bound to the support. The ligand may be chosen from the group consisting of nucleic acids, peptides, polypeptides, antibodies and aptamers and is, for example, present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

The term "amount" as used herein encompasses the absolute amount of a polypeptide or peptide, the relative amount or concentration of the said polypeptide or peptide as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations. According to exemplary embodiments of the subject invention, the determination of an "amount" is performed by the disclosed system, whereby a computing device determines the "amount" based on contacting and measuring steps performed by one or more analyzer units of said system.

The term "calculating a first ratio" or "calculating a second ratio" as referred to herein relates to calculating a ratio of the amount of sFlt-1 or Endoglin and the amount of PlGF by dividing the said amounts or by carrying out any other comparable mathematical calculation which puts into a relation the amount of sFlt-1 or Endoglin towards the amount of PlGF. According to embodiments of the instant disclosure, the amount of sFlt-1 or Endoglin is divided by the amount of PlGF in order to calculate the ratio. This calculation is carried out for the respective amounts determined in the said first and the said second sample separately yielding the first and the second ratio, respectively.

The term "comparing" as used herein encompasses comparing the first ratio to the second ratio as defined above. It is to be understood that comparing as used herein refers to any kind of comparison made between the value calculated for the first ratio with the value calculated for the second ratio. An increased risk for developing preeclampsia has been found in the studies underlying the present invention to correlate with an increase of the value of the first ratio by a factor of about 3 or more for the value of the second ratio. The comparison referred to in the method of the present invention may be carried out manually or by a computing device (e.g., of a system disclosed herein).

The comparison referred to in step (c) of the method of the present invention may be carried out manually or computer assisted. The value of the ratios can be, e.g., compared to each other and the said comparison can be automatically carried out by a computer program executing an algorithm for the comparison. As a result of the comparison of the values, a slope value is obtained which indicates the factor by which the second ratio value differs from the first ratio value. In a further step of the comparison, it is determined whether the said slope value is equal, larger or less than the factor 3. If the slope value is about 3 or larger (i.e., when an increase of about 200% or more is observed), a risk for developing preeclampsia within a short period of time will be diagnosed ("rule-in"). Similarly, a slope value below factor 3 (i.e., when an increase of less than 200%, an essentially unchanged value or a decrease is observed) shall indicate that the subject is not at risk of developing preeclampsia within a short period of time will be diagnosed ("rule-out").

Said evaluation of the result of the comparison of the first and second ratio values can be carried out automatically as well. The computer program carrying out the said evaluation will provide the desired assessment in a suitable output format. For example, a result of a comparison may be given as raw data (absolute or relative amounts), and in some cases as an indicator in the form of a word, phrase, symbol, or numerical value which may be indicative of a particular diagnosis. Said rule-in and/or rule-out diagnosis may be provided by the computing device of a system disclosed herein based on said comparison of the calculated ratio to a first or second ratio as described herein. For example, a computing device of a system may provide an indicator, in the form of a word, symbol, or numerical value which is indicative of one of a rule-in or rule-out diagnosis.

The term "about" in the context of the present invention means +/−20%, +/10%, +/−5%, +/−2% or +/−1% from the indicated parameters or values. This also takes into account usual deviations caused by measurement techniques and the like.

Advantageously, it has been found in the studies underlying the present invention that a strong increase of the ratio of the amounts of sFlt-1 or Endoglin and PlGF (sFlt1/PlGF or Endoglin/PlGF ratio) in a pregnant subject which shows no or limited clinically apparent symptoms of preeclampsia at the time when the samples which are investigated have been taken is an indicator for an imminent preeclampsia, i.e., the development of preeclampsia within a short period of a few weeks, and/or imminent HELLP syndrome. Further, it has been found that the preeclampsia developed by the said subjects being at risk is usually preeclampsia of the more severe early-onset-preeclampsia type. In particular, it was found that an increase by a factor of about 3 or more is a reliable and predictive indicator for the aforementioned imminent preeclampsia operating with a reasonable sensitivity and a specificity of more than 98%. A weaker increase, however, did not correlate very well with the development of imminent preeclampsia. Remarkably, the strong increase as specified above was predictive regardless the actual absolute amounts or ratios of the biomarkers.

Thanks to the present invention, it is possible to more reliably diagnose the risk for imminent preeclampsia, in particular, imminent early-onset-preeclampsia, based on a reliable indicator which appears to be independent on the actual absolute amounts of the aforementioned biomarkers found in a subject. Moreover, the time consuming, expensive and cumbersome diagnostic measures such as the current scoring systems can be avoided when applying the method of the invention as an aid for diagnosis. Health care management shall greatly benefit from the method of the present invention since the need for intensive and special care required for pregnant females suffering from preeclampsia can be better estimated and be taken into account for health care management purposes.

It is to be understood that the definitions and explanations of the terms made above and below apply accordingly for all embodiments described in this specification and the accompanying claims.

According to embodiments of the instant disclosure methods of the present invention, include preeclampsia being early-onset-preeclampsia. Accordingly, the method of the invention allows for diagnosing whether a subject is at increased risk for developing early-onset-preeclampsia within a short period of time, in particular if the pregnant subject is between week 15 and week 30 of gestation. As discussed before, early-onset-preeclampsia usually has more severe consequences than late-onset-preeclampsia and the subjects suffering therefrom need supportive measures in order to ameliorate the consequences of the preeclampsia. For example, subjects at risk can be admitted to a hospital with maternal fetal intensive care unit at an early stage.

In some embodiments of the method of the present invention, said method further comprises recommending at least one supportive measure for preeclampsia, if it is diagnosed that the subject is at increased risk for developing preeclampsia within a short period of time.

The term "recommending" as used herein means establishing a proposal for a supportive measure or combinations thereof which could be applied to the subject. However, it is to be understood that applying the actual therapy, whatsoever, is not comprised by the term.

As discussed before, a subject suffering from preeclampsia requires particular medical care. Thus, if a subject is diagnosed to be at risk of developing preeclampsia, such a diagnosis can help to establish suitable supportive measures for the subject in advance, i.e., before the preeclampsia becomes clinically apparent. According to embodiments of the instant disclosure, said at least one supportive measure is selected from the group consisting of: close monitoring, hospitalization, administration of blood pressure reducing agents, and/or life style recommendations. With respect to the fetus, betamethasone administration may be recommended as well in order to improve the respiratory functions in the new-born in case of a later premature delivery.

Embodiment of the present invention further relates to a method for differentiating between a pregnant subject being at risk of developing early-onset-preeclampsia and a pregnant subject being not at risk of developing early-onset-preeclampsia comprising: a) determining the amounts of the biomarkers sFlt-1 or Endoglin and PlGF in a first and a second sample of said subject, wherein said first sample has been obtained prior to said second sample; b) calculating a first ratio from said amounts of sFlt-1 or Endoglin and PlGF determined in the first sample and a second ratio from said amounts of sFlt-1 or Endoglin and PlGF determined in the second sample; c) comparing the value of the said first and the said second ratio, whereby a subject being at risk for developing early-onset-preeclampsia is diagnosed if the value of the second ratio is increased compared to the value of the first ratio by a factor of at least about 3. In some cases, said early-onset-preeclampsia develops within a short period of time as set forth elsewhere herein in detail. According to embodiments, the said second sample has been obtained no later than about week 30 of gestation, i.e., prior or at week 30 of gestation.

As discussed above already, the reliable identification of subjects which are at risk for developing early-onset-preeclampsia is a decisive task in health management. In particular, special care is required for pregnant females suffering from preeclampsia and, thanks to the present invention; the need for such care can be better estimated and be taken into account for health care management purposes. In particular, the aforementioned method even allows identifying an early-onset type of preeclampsia if the second sample is obtained around week 30 of gestation. It will be understood that preeclampsia in a subject which exhibits no or only limited symptoms of preeclampsia until week 30 of gestation, i.e., when the second sample has been taken, will in all likelihood be diagnosed as non-early-onset preeclampsia since the clinically apparent preeclampsia will normally occur after week 34 of gestation. Since the aforementioned method takes into account the dynamics of biomarkers, it allows for more reliably diagnosing the proper type of preeclampsia.

The present invention, in general, contemplates the use of the biomarkers sFlt-1 or Endoglin and PlGF or detection agents which specifically bind thereto in a first and a second sample of a pregnant subject for diagnosing whether said subject is at risk for developing preeclampsia within a short period of time. According to embodiments of the instant disclosure, the biomarkers or detection agents therefore can be used, as indicated in the aforementioned method, for diagnosing whether said subject is at risk for developing preeclampsia within a short period of time in a pregnant subject. According to embodiments of the instant disclosure, ratios of sFlt-1 or Endoglin and PlGF shall be calculated for the first and the second sample and the ratios shall subsequently be compared to each other in order to determine the factor of increase or alteration between the two ratios, wherein an increase of by a factor of about 3 or more is to be used as an indicator for a subject being at risk for developing preeclampsia within a short period of time.

Moreover, the present invention also contemplates, in general, the use of the biomarkers sFlt-1 or Endoglin and PlGF or detection agents which specifically bind thereto in a first and a second sample of a pregnant subject for differentiating between a pregnant subject being at risk of developing early-onset-preeclampsia and a pregnant subject being not at risk of developing early-onset-preeclampsia.

According to embodiments of the instant disclosure, the biomarkers or detection agents therefore can be used as indicated in the aforementioned method for differentiating between a pregnant subject being at risk of developing early-onset-preeclampsia and a pregnant subject being not at risk of developing early-onset-preeclampsia. For example, ratios of sFlt-1 or Endoglin and PlGF shall be calculated for the first and the second sample and the ratios shall subsequently be compared to each other in order to determine the factor of increase or alteration between the two ratios, wherein an increase of by a factor of about 3 or more is to be used as an indicator for a subject being at risk for developing early-onset-preeclampsia.

According to embodiments of the instant disclosure, a method for establishing an aid for optimizing a risk assessment based on a clinical prediction rule for classifying pregnant subjects is disclosed, said method comprising: a) obtaining a first ratio by (i) bringing a first sample into contact with a detection agent (detection agents) that specifically bind(s) to sFlt-1, Endoglin, and/or PlGF for a time sufficient to allow for the formation of a complex of the said detection agent and the markers from the sample, (ii) measuring the amount of the formed complex(es), wherein the said amount of the formed complex(es) is proportional to the amount of the markers present in the sample, (iii) transforming the amount of the formed complex(es) into amounts of the markers reflecting the amounts of the markers present in the sample, and (iv) calculating a first ratio from said amounts of sFlt-1 or Endoglin and PlGF determined said first sample; b) obtaining a second ratio by (i) bringing a second sample into contact with a detection agent (detection agents) that specifically bind(s) to sFlt-1, Endoglin, and/or PlGF for a time sufficient to allow for the formation of a complex of the said detection agent and the markers from the sample, (ii) measuring the amount of the formed complex(es), wherein the said amount of the formed complex(es) is proportional to the amount of the markers present in the sample, (iii) transforming the amount of the formed complex(es) into amounts of the markers reflecting the amounts of the markers present in the sample, and (iv) calculating a second ratio from said amounts of sFlt-1 or Endoglin and PlGF determined said second sample; c) comparing said first ratio to a second ratio; and d) establishing an aid for optimizing a risk assessment based on a clinical prediction rule for classifying pregnant subjects based on the result of the comparison made in step c).

According to embodiments of the instant disclosure, a system for establishing an aid for optimizing a risk assessment based on a clinical prediction rule for classifying pregnant subjects is contemplated, comprising: a) an analyzer unit configured to contact, in vitro, a portion of a second sample from a pregnant subject with a ligand comprising specific binding affinity for sFlt-1 and/or Endoglin and configured to contact, in vitro, a portion of a sample from a pregnant subject with a ligand comprising specific binding affinity for PlGF, b) an analyzer unit configured to detect a signal from the portions of the sample from the subject contacted with the ligands, c) a computing device having a processor and in operable communication with said analysis units, and d) a non-transient machine readable media including a plurality of instruction executable by a processor, the instructions, when executed, calculating an amount of sFlt-1 and/or Endoglin, calculating an amount of PlGF, calculating a second ratio from said amounts of sFlt-1 or Endoglin and PlGF determined in the sample and comparing the ratio thus calculated with a first ratio obtained from a first sample, thereby optimizing the risk assessment based on the clinical prediction rule for classifying pregnant subjects.

A suitable detection agent may be, in an aspect, an antibody which specifically binds to the at least one marker, i.e. a detection agent which binds to sFlt-1, to Endoglin, or to PlGF, in a sample of a subject to be investigated by the method of the invention. Another detection agent that can be applied, in an aspect, may be an aptamere which specifically binds to the at least one marker in the sample. In yet an aspect the, sample is removed from the complex formed between the detection agent and the at least one marker prior to the measurement of the amount of formed complex. Accordingly, in an aspect, the detection agent may be immobilized on a solid support. In yet another aspect, the sample can be removed from the formed complex on the solid support by applying a washing solution. The formed complex shall be proportional to the amount of the at least one marker present in the sample. It will be understood that the specificity and/or sensitivity of the detection agent to be applied defines the degree of proportion of at least one marker comprised in the sample which is capable of being specifically bound. Further details on how the determination can be carried out are also found elsewhere herein. The amount of formed complex shall be transformed into an amount of at least one marker reflecting the amount indeed present in the sample. Such an amount, in an aspect, may be essentially the amount present in the sample or may be, in another aspect, an amount which is a certain proportion thereof due to the relationship between the formed complex and the amount present in the original sample. In yet an aspect of the aforementioned method, step a) may be carried out by an analyzer unit, in an aspect, an analyzer unit as defined elsewhere herein.

The aid for optimizing a risk assessment is established based on the comparison carried out in step d) by allocating the subject either into a group of subjects having an increased risk or decreased risk as set forth herein elsewhere. As discussed elsewhere herein already, the allocation of the investigated subject must not be correct in 100% of the investigated cases. Moreover, the groups of subjects into which the investigated subject is allocated are artificial groups in that they are established based on statistical considerations, i.e. a certain preselected degree of likelihood based on which the method of the invention shall operate. In an aspect of the invention, the aid for optimizing a risk assessment is established automatically, e.g., assisted by a computing device or the like, as described and disclosed herein.

According to embodiments of the instant disclosure, said method further comprises a step of recommending and/or managing the subject according to the result established in step d) as set forth elsewhere herein in detail, and/or adapting intensiveness of disease monitoring.

In another aspect of the invention, a system for establishing an aid for optimizing a risk assessment based on a clinical prediction rule for classifying subjects with pneumonia, is contemplated, comprising: a)an analyzer unit configured to contact, in vitro, a portion of a second sample from a pregnant subject with a ligand comprising specific binding affinity for sFlt-1 and/or Endoglin and configured to contact, in vitro, a portion of a sample from a pregnant subject with a ligand comprising specific binding affinity for PlGF, b)an analyzer unit configured to detect a signal from the portions of the sample from the subject contacted with the ligands, c)a computing device having a processor and in operable communication with said analysis units, and d) a non-transient machine readable media including a plurality of instruction executable by a processor, the instructions, when executed, calculating an amount of sFlt-1 and/or Endoglin, calculating an amount of PlGF, calculating a second ratio from said amounts of sFlt-1 or Endoglin and PlGF determined in the sample and comparing the ratio thus calculated with a first ratio obtained from a first sample, thereby optimizing the risk assessment based on the clinical prediction rule for classifying pregnant subjects.

According to embodiments of the instant disclosure, a system for optimizing a risk assessment based on a clinical prediction rule for classifying pregnant is disclosed. Examples of systems include clinical chemistry analyzers, coagulation chemistry analyzers, immunochemistry analyzers, urine analyzers, nucleic acid analyzers, used to detect the result of chemical or biological reactions or to monitor the progress of chemical or biological reactions. More specifically, exemplary systems of the instant disclosure may include Roche ELECSYS™ Systems and COBAS® e Immunoassay Analyzers, Abbott ARCHITECT™ and AXSYM™ Analyzers, Siemens CENTAUR™ and IMMULITE™ Analyzers, and Beckman Coulter UNICEl™ and ACESS™ Analyzers, or the like.

Embodiments of the system may include one or more analyzer units utilized for practicing the subject disclosure. The analyzer units of the system disclosed herein are in operable communication with the computing device disclosed herein through any of a wired connection, Bluetooth, LANS, or wireless signal, as are known. Additionally, according to the instant disclosure, an analyzer unit may comprise a stand-alone apparatus, or module within a larger instrument, which performs one or both of the detection, e.g. qualitative and/or quantitative evaluation of samples for diagnostic purpose. For example, an analyzer unit may perform or assist with the pipetting, dosing, mixing of samples and/or reagents. An analyzer unit may comprise a reagent holding unit for holding reagents to perform the assays. Reagents may be arranged for example in the form of containers or cassettes containing individual reagents or group of reagents, placed in appropriate receptacles or positions within a storage compartment or conveyor. Detection reagents may also be in immobilized form on a solid support which are contacted with the sample. Further, an analyzer unit may include a process and/or detection component which is optimizable for specific analysis.

According to some embodiments, an analyzer unit may be configured for optical detection of an analyte, for example a marker, with a sample. An exemplary analyzer unit configured for optical detection comprises a device configured for converting electro-magnetic energy into an electrical signal, which includes both single and multi-element or array optical detectors. According to the present disclosure, an optical detector is capable of monitoring an optical electromagnetic signal and providing an electrical outlet signal or response signal relative to a baseline signal indicative of the presence and/or concentration of an analyte in a sample being located in an optical path. Such devices may also include, for example, photodiodes, including avalanche photodiodes, phototransistors, photoconductive detectors, linear sensor arrays, CCD detectors, CMOS detectors, including CMOS array detectors, photomultipliers, and photomultiplier arrays. According to certain embodiments, an optical detector, such as a photodiode or photomultiplier, may contain additional signal conditioning or processing electronics. For example, an optical detector may include at least one pre-amplifier, electronic filter, or integrated circuit. Suitable pre-preamplifiers include, for example, integrating, transimpedance, and current gain (current mirror) preamplifiers.

Additionally, one or more analyzer unit according to the instant disclosure may comprise a light source for emitting light. For example, a light source of an analyzer unit may consist of at least one light emitting element (such as a light emitting diode, an electric powered radiation source such as an incandescent lamp, an electroluminescent lamp, a gas discharge lamp, a high-intensity discharge lamp, a laser) for measuring analyte concentrations with a sample being tested or for enabling an energy transfer (for example, through florescent resonance energy transfer or catalyzing an enzyme).

Further, an analyzer unit of the system may include one or more incubation units (for example, for maintaining a sample or a reagent at a specified temperature or temperature range). In some embodiments, an analyzer unit may include a thermocycler, include a real-time thermocycler, for subjecting a sample to repeated temperature cycles and monitoring a change in the amount of an amplification product with the sample.

Additionally, an analyzer unit of the system disclosed herein may comprise, or be operationally connected to, a reaction vessel or cuvette feeding unit. Exemplary feeding units include liquid processing units, such as a pipetting unit, to deliver samples and/or reagents to the reaction vessels. The pipetting unit may comprise a reusable washable needle, e.g. a steel needle, or disposable pipette tips. The analyzer unit may further comprise one or more mixing units, for example a shaker to shake a cuvette comprising a liquid, or a mixing paddle to mix liquids in a cuvette, or reagent container.

The present invention further relates to a device adapted for diagnosing whether a pregnant subject is at risk for developing preeclampsia within a short period of time by carrying out the aforementioned method comprising: a) an analyzing unit comprising a detection agent which specifically binds to sFlt-1 and/or Endoglin and a detection agent which specifically binds to PIGF, said unit being adapted for determining the amount of sFlt-1 and/or Endoglin and the amount of PIGF in a first and a second sample of a pregnant subject; and b) an evaluation unit comprising a data processor having implemented an algorithm for carrying out the following steps of: i) calculating a first ratio from said amounts of sFlt-1 or Endoglin and PIGF determined in the first sample and a second ratio from said amounts of sFlt-1 or Endoglin and PIGF determined in the second sample; and ii) comparing the value of the said first and the said second ratio, whereby a subject being at risk for developing preeclampsia within a short period of time is diagnosed if the value of the second ratio is increased compared to the value of the first ratio by a factor of at least about 3.

The term "device" as used herein relates to a system comprising the aforementioned units operatively linked to each other as to allow the diagnosis according to the methods of the invention. Exemplary detection agents which can be used for the analyzing unit are disclosed elsewhere herein. The analyzing unit (or analyzer unit), for example, may comprise said detection agents in immobilized form on a solid support which is to be contacted to the sample comprising the biomarkers the amount of which is to be determined. Moreover, the analyzing unit can also comprise a detector which determines the amount of detection agent which is specifically bound to the biomarker(s). The determined amount can be transmitted to the evaluation unit. Said evaluation unit comprises a data processing element, such as a computer, with an implemented algorithm for carrying out a calculation of ratios, a comparison of said calculated ratios and an evaluation of the result of the comparison by implementation of an computer based algorithm carrying out the steps of the method of the present invention set forth elsewhere herein in detail. The results may be given as output of parametric diagnostic raw data. It is to be understood that these data will usually need interpretation by the clinician. However, also envisage are expert system devices wherein the output comprises processed diagnostic raw data the interpretation of which does not require a specialized clinician.

According to some embodiments of the instant disclosure, an algorithm for carrying out a comparison between a first ratio and a second ratio disclosed herein is embodied and performed by executing the instructions. The results may be given as output of parametric diagnostic raw data or as absolute or relative amounts. According to various embodiments of the system disclosed herein, a "diagnosis" may be provided by the computing device of a system disclosed herein based on said comparison of the calculated ratios. For example, a computing device of a system may provide an indicator, in the form of a word, symbol, or numerical value which is indicative of a particular diagnosis.

The present invention further relates to a device adapted for differentiating between a pregnant subject being at risk of developing early-onset-preeclampsia and a pregnant subject being not at risk of developing early-onset-preeclampsia by carrying out the aforementioned method comprising: a) an analyzing unit comprising a detection agent which specifically binds to sFlt-1 and/or Endoglin and a detection agent which specifically binds to PIGF, said unit being adapted for determining the amount of sFlt-1 and/or Endoglin and the amount of PIGF in a first and a second sample of a pregnant subject; and b) an evaluation unit comprising a data processor having implemented an algorithm for carrying out the following steps of: i) calculating a first ratio from said amounts of sFlt-1 or Endoglin and PIGF determined in the first sample and a second ratio from said amounts of sFlt-1 or Endoglin and PIGF determined in the second sample; and ii) comparing the value of the said first and the said second ratio, whereby a subject being at risk for developing early-onset-preeclampsia is diagnosed if the value of the second ratio is increased compared to the value of the first ratio by a factor of at least about 3.

Furthermore, encompassed by the invention is a kit adapted for carrying out the aforementioned method for diagnosing whether a pregnant subject is at risk for developing preeclampsia within a short period of time comprising detection agents for determining the amounts of the biomarkers sFlt-1 or Endoglin and PlGF as well as instructions for carrying out the said method.

The term "kit" as used herein refers to a collection of the aforementioned components, for example, provided in separately or within a single container. The container also comprises instructions for carrying out the method of the present invention. These instructions may be in the form of a manual or may be provided by a computer program code which is capable of carrying out the calculations and comparisons referred to in the methods of the present invention and to establish a diagnosis accordingly when implemented on a computer or a data processing device. The computer program code may be provided on a data storage medium or device such as an optical storage medium (e.g., a Compact Disc) or directly on a computer or data processing device. Moreover, the kit may, for example, comprise standard amounts for the biomarkers as described elsewhere herein for calibration purposes.

The invention further encompasses a kit adapted for carrying out the aforementioned method for differentiating between a pregnant subject being at risk of developing early-onset-preeclampsia and a pregnant subject being not at risk of developing early-onset-preeclampsia comprising detection agents for determining the amounts of the biomarkers sFlt-1 or Endoglin and PlGF as well as instructions for carrying out the said method.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

Illustrative Embodiments

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. A method for diagnosing whether a pregnant subject is at risk for developing preeclampsia within a short period of time comprising:
    a) determining the amounts of the biomarkers sFlt-1 or Endoglin and PlGF in a first and a second sample of said subject, wherein said first sample has been obtained prior to said second sample;
    b) calculating a first ratio from said amounts of sFlt-1 or Endoglin and PlGF determined in the first sample and a second ratio from said amounts of sFlt-1 or Endoglin and PlGF determined in the second sample;
    c) comparing the value of the said first and the said second ratio, whereby a subject being at risk for developing preeclampsia within a short period of time is diagnosed if the value of the second ratio is increased compared to the value of the first ratio by a factor of at least about 3.
2. The method of embodiment 1, wherein said first sample has been obtained about 4 to about 5 weeks prior to the said second sample.
3. The method of embodiments 1 or 2, wherein said pregnant subject is between about week 15 and about week 34 of gestation, preferably, between about week 15 and about week 30 of gestation.
4. The method of any one of embodiments 1 to 3, wherein said short period of time is a period of time less than 4 weeks, preferably, between about 2 to about 3 weeks.
5. The method of any one of embodiments 1 to 4, wherein said preeclampsia is early-onset-preeclampsia.
6. The method of any one of embodiments 1 to 5, wherein said method further comprises recommending at least one supportive measure for preeclampsia, if it is diagnosed that the subject is at increased risk for developing preeclampsia within a short period of time.
7. The method of embodiment 6, wherein said at least one supportive measure is selected from the group consisting of: close monitoring, hospitalization, administration of blood pressure reducing agents and/or life style recommendations.
8. A method for differentiating between a pregnant subject being at risk of developing early-onset-preeclampsia and a pregnant subject being not at risk of developing early-onset-preeclampsia comprising:
    a) determining the amounts of the biomarkers sFlt-1 or Endoglin and PlGF in a first and a second sample of said subject, wherein said first sample has been obtained prior to said second sample;
    b) calculating a first ratio from said amounts of sFlt-1 or Endoglin and PlGF determined in the first sample and a second ratio from said amounts of sFlt-1 or Endoglin and PlGF determined in the second sample;
    c) comparing the value of the said first and the said second ratio, whereby a subject being at risk for developing early-onset-preeclampsia is diagnosed if the value of the second ratio is increased compared to the value of the first ratio by a factor of at least about 3.
9. The method of embodiment 8, wherein said first sample has been obtained about 4 to about 5 weeks prior to the said second sample.
10. The method of embodiment 8 or 9, wherein said pregnant subject is between about week 15 and about week 34 of gestation, preferably, between about week 15 and about week 30 of gestation.
11. The method of any one of embodiments 1 to 10, wherein said first and said second sample is a blood, serum or plasma sample.
12. Use of the biomarkers sFlt-1 or Endoglin and PlGF or detection agents which specifically bind thereto in a first and a second sample of a pregnant subject for diagnosing whether said subject is at risk for developing preeclampsia within a short period of time.
13. Use of the biomarkers sFlt-1 or Endoglin and PlGF or detection agents which specifically bind thereto in a first and a second sample of a pregnant subject for differentiating between a pregnant subject being at risk of developing early-onset-preeclampsia and a pregnant subject being not at risk of developing early-onset-preeclampsia.

14. A device adapted for diagnosing whether a pregnant subject is at risk for developing preeclampsia within a short period of time by carrying out the method of any one of embodiments 1 to 7 and 11 comprising:
    a) an analyzing unit comprising a detection agent which specifically binds to sFlt-1 and/or Endoglin and a detection agent which specifically binds to PIGF, said unit being adapted for determining the amount of sFlt-1 and/or Endoglin and the amount of PIGF in a first and a second sample of a pregnant subject; and
    b) an evaluation unit comprising a data processor having implemented an algorithm for carrying out the following steps of:
        i) calculating a first ratio from said amounts of sFlt-1 or Endoglin and PIGF determined in the first sample and a second ratio from said amounts of sFlt-1 or Endoglin and PIGF determined in the second sample; and
        ii) comparing the value of the said first and the said second ratio, whereby a subject being at risk for developing preeclampsia within a short period of time is diagnosed if the value of the second ratio is increased compared to the value of the first ratio by a factor of at least about 3.

15. A device adapted for differentiating between a pregnant subject being at risk of developing early-onset-preeclampsia and a pregnant subject being not at risk of developing early-onset-preeclampsia by carrying out the method of any one of embodiments 8 to 11 comprising:
    a) an analyzing unit comprising a detection agent which specifically binds to sFlt-1 and/or Endoglin and a detection agent which specifically binds to PIGF, said unit being adapted for determining the amount of sFlt-1 and/or Endoglin and the amount of PIGF in a first and a second sample of a pregnant subject; and
    b) an evaluation unit comprising a data processor having implemented an algorithm for carrying out the following steps of:
        i) calculating a first ratio from said amounts of sFlt-1 or Endoglin and PIGF determined in the first sample and a second ratio from said amounts of sFlt-1 or Endoglin and PIGF determined in the second sample; and
        ii) ii) comparing the value of the said first and the said second ratio, whereby a subject being at risk for developing early-onset-preeclampsia is diagnosed if the value of the second ratio is increased compared to the value of the first ratio by a factor of at least about 3.

16. A kit adapted for carrying out the method of any one of embodiments 1 to 7 and 11 comprising detection agents for determining the amounts of the biomarkers sFlt-1 or Endoglin and PIGF as well as instructions for carrying out the said method.

17. A kit adapted for carrying out the method of any one of embodiments 8 to 11 comprising detection agents for determining the amounts of the biomarkers sFlt-1 or Endoglin and PIGF as well as instructions for carrying out the said method.

EXAMPLES

Example 1: Measurement of Blood Levels of PIGF, sFLT1 and Endoglin

Blood levels of sFLT1, PIGF and Endoglin were determined using the commercially available immunoassays. In particular; the following assays have been used:

sFlt1 was determined with sandwich immunoassays using analysers from the Roche Elecsys™- or cobas e™-series. The assay comprises two monoclonal antibodies specific for the respective polypeptide. The first of these antibodies is biotinylated and the second one is labelled with a Tris(2,2'-bipyridyl)ruthenium(II)-complex. In a first incubation step both antibodies are incubated with the sample. A sandwich complex comprising the peptide to be determined and the two different antibodies is formed. In a next incubation step streptavidin-coated beads are added to this complex. The beads bind to the sandwich complexes. The reaction mixture is then aspirated into a measuring cell where the beads are magnetically captured on the surface of an electrode. The application of a voltage then induces a chemiluminescent emission from the ruthenium complex which is measured by a photomultiplier. The emitted amount of light is dependent on the amount of sandwich complexes on the electrode. The sFlt-1 test is commercially available from Roche Diagnostics GmbH, Mannheim, Germany. Further details on the assay are found in the package insert. The measuring range of sFlt1 includes amounts between 10 to 85,000 pg/ml.

Endoglin was measured using the Quantikine™ Human Endoglin/CD105 immunoassay which is commercially available from R&D Systems, Inc, Minneapolis, US. This assay employs the quantitative sandwich enzyme immunoassay technique. A monoclonal antibody specific for Endoglin has been pre-coated onto a microplate. Standards and samples are pipetted into the wells and any Endoglin present is bound by the immobilized antibody. After washing away any unbound substances, an enzyme-linked monoclonal antibody specific for Endoglin is added to the wells. Following a wash to remove any unbound antibody-enzyme reagent, a substrate solution is added to the wells and color develops in proportion to the amount of Endoglin bound in the initial step. The color development is stopped and the intensity of the color is measured. Further details on the assay are found in the package insert. The measuring range of Endoglin includes amounts between 0.001 ng/L to 10 ng/ml.

PIGF was tested using two PIGF specific antibodies in an sandwich immunoassay which is carried out on an ELECSYS™- or COBAS E™ series analyzer (see above for details). The PIGF test is commercially available from Roche Diagnostics GmbH, Mannheim, Germany. Further details on the assay are found in the package insert. The measuring range of PIGF includes amounts of 3 to 10,000 pg/ml.

Example 2: Analysis of the Biomarkers sFlt-1 and PIGF in Outcome Patients Which Developed Preeclampsia and in Healthy Controls A total number of 286 patients recruited at different sites in Europe were investigated. Included in the study were pregnant women at a gestational age of at least 15+0 and at most 30+0 weeks. Reference values for the sFlt-1/PIGF ratio are usually slightly decreasing until about week 28, hence a physiological increase of values in this time interval was not to be expected. The diagnosis at every patient visit included in the study was "no Preeclampsia or HELLP (PE/HELLP)" or "suspected PE/HELLP". The diagnosis at outcome of these patients can be PE/HELLP and it was analysed here if increasing values are an indicator for an imminent diagnosis of PE/HELLP. Every woman contributed two visits: her last visit before week 30+0 (visit 2) and one earlier visit (visit 1). In case of more than one options for visit 1, that one is selected, which was nearest to 3 weeks before visit 2.

Blood levels of PlGF and sFlt-1 were determined as described in Example 1, above, and evaluated. The results of were as summarized in the following Tables 1 to 11:

TABLE 1

| Diagnosis at final outcome | |
|---|---|
| PE/HELLP | No PE/HELLP |
| N  37 | 249 |

TABLE 2

Gestational age at visit 1

| | Min. | Qu.−25 | Median | Qu.−75 | Max. | Mean | SD | N |
|---|---|---|---|---|---|---|---|---|
| PE/HELLP | 16.14 | 20.00 | 21.71 | 24.57 | 28.00 | 21.83 | 3.43 | 37 |
| No PE/HELLP | 15.00 | 20.29 | 21.86 | 24.14 | 28.57 | 21.70 | 3.02 | 249 |

TABLE 3

Gestational age at visit 2

| | Min. | Qu.−25 | Median | Qu.−75 | Max. | Mean | SD | N |
|---|---|---|---|---|---|---|---|---|
| PE/HELLP | 20.29 | 26.71 | 27.86 | 28.86 | 30.00 | 27.27 | 2.52 | 37 |
| No PE/HELLP | 19.14 | 25.57 | 27.14 | 28.71 | 30.00 | 26.78 | 2.41 | 249 |

TABLE 4

Days between visits

| | Min. | Qu.−25 | Median | Qu.−75 | Max. | Mean | SD | N |
|---|---|---|---|---|---|---|---|---|
| PE/HELLP | 14.00 | 28.00 | 34.00 | 47.00 | 90.00 | 38.11 | 17.33 | 37 |
| No PE/HELLP | 5.00 | 28.00 | 32.00 | 41.00 | 96.00 | 35.53 | 14.40 | 249 |

TABLE 5 sFlt-1/PlGF ratio at visit 1

| | Min. | Qu.−25 | Median | Qu.−75 | Max. | Mean | SD | N |
|---|---|---|---|---|---|---|---|---|
| PE/HELLP | 0.81 | 5.10 | 10.46 | 19.70 | 225.23 | 24.36 | 45.37 | 37 |
| No PE/HELLP | 0.50 | 3.10 | 5.24 | 8.68 | 41.38 | 6.74 | 5.53 | 249 |

TABLE 6 sFlt-1PlGF ratio at visit 2

| | Min. | Qu.−25 | Median | Qu.−75 | Max. | Mean | SD | N |
|---|---|---|---|---|---|---|---|---|
| PE/HELLP | 1.48 | 4.58 | 9.77 | 88.96 | 856.23 | 72.86 | 155.23 | 37 |
| No PE/HELLP | 0.44 | 1.85 | 3.25 | 5.30 | 40.67 | 4.94 | 5.72 | 249 |

TABLE 7

Absolute change of the sFlt-1/PlGF ratio between visits

| | Min. | Qu.−25 | Median | Qu.−75 | Max. | Mean | SD | N |
|---|---|---|---|---|---|---|---|---|
| PE/HELLP | −17.94 | −2.16 | 0.09 | 40.25 | 742.25 | 48.50 | 131.27 | 37 |
| No PE/HELLP | −21.40 | −3.39 | −1.59 | −0.36 | 25.60 | −1.81 | 4.61 | 249 |

TABLE 8

Percentage gain of sFlt-1/PlGF ratio

|  | Min. | Qu.–25 | Median | Qu.–75 | Max. | Mean | SD | N |
|---|---|---|---|---|---|---|---|---|
| PE/HELLP | −75.84 | −36.34 | 5.72 | 245.74 | 1691.91 | 182.84 | 372.92 | 37 |
| No PE/HELLP | −92.11 | −51.93 | −35.04 | −10.63 | 309.43 | −24.14 | 49.77 | 249 |

TABLE 9

Listing of patients with a gain of sFlt-1/PlGF ratio of 100% or more

| Ratio 1 | Ratio 2 | Gain | Visit 1 | Visit 2 | PE/HELLP |
|---|---|---|---|---|---|
| 10.13 | 20.42 | 101.7% | 25 w + 4 d | 29 w + 4 d | No |
| 16.58 | 33.89 | 104.5% | 26 w + 0 d | 28 w + 6 d | No |
| 4.69 | 9.77 | 108.5% | 20 w + 4 d | 28 w + 2 d | Yes |
| 156.22 | 340.90 | 118.2% | 16 w + 6 d | 20 w + 6 d | Yes |
| 5.82 | 13.06 | 124.2% | 17 w + 1 d | 30 w + 0 d | Yes |
| 8.00 | 18.31 | 128.7% | 19 w + 6 d | 27 w + 6 d | Yes |
| 6.28 | 14.39 | 129% | 24 w + 6 d | 29 w + 0 d | No |
| 2.34 | 5.43 | 131.9% | 23 w + 1 d | 27 w + 4 d | Yes |
| 9.85 | 23.02 | 133.8% | 24 w + 1 d | 29 w + 1 d | No |
| 3.39 | 8.04 | 137.1% | 24 w + 1 d | 28 w + 1 d | No |
| 1.21 | 3.76 | 210.3% | 24 w + 3 d | 28 w + 5 d | No |
| 5.59 | 18.20 | 225.4% | 24 w + 0 d | 27 w + 6 d | Yes |
| 37.29 | 128.92 | 245.7% | 26 w + 0 d | 29 w + 1 d | Yes |
| 1.71 | 5.95 | 247.2% | 24 w + 3 d | 28 w + 3 d | No |
| 13.62 | 53.87 | 295.5% | 28 w + 0 d | 30 w + 0 d | Yes |
| 8.27 | 33.87 | 309.4% | 23 w + 6 d | 29 w + 6 d | No |
| 20.60 | 88.96 | 331.9% | 25 w + 5 d | 29 w + 4 d | Yes |
| 32.30 | 144.39 | 347% | 25 w + 1 d | 29 w + 1 d | Yes |
| 30.24 | 138.30 | 357.4% | 24 w + 4 d | 28 w + 4 d | Yes |
| 113.98 | 856.23 | 651.2% | 25 w + 1 d | 27 w + 6 d | Yes |
| 19.70 | 167.62 | 750.8% | 24 w + 5 d | 28 w + 0 d | Yes |
| 13.86 | 124.57 | 799% | 20 w + 0 d | 27 w + 1 d | Yes |
| 20.99 | 239.20 | 1039.8% | 25 w + 6 d | 29 w + 6 d | Yes |
| 0.81 | 14.50 | 1691.9% | 21 w + 0 d | 27 w + 0 d | Yes |

TABLE 10

Categorized gain of sFlt-1/PlGF ratio vs. final outcome

|  | PE/HELLP | [%] | No PE/HELLP | [%] |
|---|---|---|---|---|
| Gain <0% | 17 | 45.9 | 201 | 80.7 |
| Gain 0-100% | 4 | 10.8 | 40 | 16.1 |
| Gain 100-200% | 5 | 13.5 | 5 | 2.0 |
| Gain >200% | 11 | 29.7 | 3 | 1.2 |
| Sum | 37 | 100.0 | 249 | 100.0 |

TABLE 11

Sens/Spec depending on gain as cutoff

| Cutoff at 100% | Sensitivity | 43.2% |
|---|---|---|
|  | Specificity | 96.% |
| Cutoff at 200% | Sensitivity | 29.7% |
|  | Specificity | 98.8% |

The present European PE study allows for the observation that a strong increase of the sFlt-1/PlGF ratio (in this proposal threefold or more) seems to be a clear indicator for an imminent PE/HELLP.

Example 3: Analysis of the Biomarkers Endoglin and PlGF in Outcome Patients Which Developed Preeclampsia and in Healthy Controls Similar patient samples as referred to in Example 2 were investigated for blood levels of PlGF and Endoglin (s-Eng) and evaluated. The results were as follows:

TABLE 12 sEng/PlGF ratio at visit 1

|  | Min. | Qu. –25 | Median | Qu. –75 | Max. | Mean | SD | N |
|---|---|---|---|---|---|---|---|---|
| PE/HELLP | 0.00 | 0.02 | 0.06 | 0.12 | 0.30 | 0.08 | 0.08 | 21 |
| No PE/HELLP | 0.01 | 0.01 | 0.02 | 0.03 | 0.09 | 0.02 | 0.02 | 16 |

TABLE 13 sEng/PlGF ratio at visit 2

|  | Min. | Qu. –25 | Median | Qu. –75 | Max. | Mean | SD | N |
|---|---|---|---|---|---|---|---|---|
| PE/HELLP | 0.00 | 0.02 | 0.08 | 0.75 | 2.76 | 0.45 | 0.68 | 21 |
| No PE/HELLP | 0.01 | 0.01 | 0.01 | 0.02 | 0.07 | 0.02 | 0.02 | 16 |

TABLE 14

Absolute change of the sEng/PlGF ratio between visits

|  | Min. | Qu. –25 | Median | Qu. –75 | Max. | Mean | SD | N |
|---|---|---|---|---|---|---|---|---|
| PE/HELLP | −71.51 | −19.28 | 117.78 | 641.20 | 1200.02 | 300.11 | 405.51 | 21 |
| No PE/HELLP | −81.01 | −51.63 | −37.34 | −21.20 | 372.91 | 1.33 | 119.40 | 16 |

TABLE 15

Percentage gain of sEng/PlGF ratio

|  | Min. | Qu. −25 | Median | Qu. −75 | Max. | Mean | SD | N |
|---|---|---|---|---|---|---|---|---|
| PE/HELLP | −71.51 | −19.28 | 117.78 | 641.20 | 1200.02 | 300.11 | 405.51 | 21 |
| No PE/HELLP | −81.01 | −51.63 | −37.34 | −21.20 | 372.91 | 1.33 | 119.40 | 16 |

TABLE 16

Listing of patients with a gain of sEng/PlGF ratio of 100% or more

| eratio 1 | eratio2 | Gain | Visit 1 | Visit 2 | PE/HELLP |
|---|---|---|---|---|---|
| 0.09 | 0.20 | 117.8% | 26 w + 0 d | 29 w + 1 d | Yes |
| 0.01 | 0.02 | 215.5% | 24 w + 3 d | 28 w + 3 d | No |
| 0.10 | 0.34 | 236% | 25 w + 5 d | 29 w + 4 d | Yes |
| 0.04 | 0.13 | 245.8% | 24 w + 0 d | 27 w + 6 d | Yes |
| 0.17 | 0.65 | 269.9% | 28 w + 0 d | 30 w + 0 d | Yes |
| 0.02 | 0.07 | 372.9% | 23 w + 6 d | 29 w + 6 d | No |
| 0.14 | 0.75 | 419.7% | 25 w + 1 d | 29 w + 1 d | Yes |
| 0.18 | 1.33 | 641.2% | 24 w + 4 d | 28 w + 4 d | Yes |
| 0.10 | 0.81 | 688.1% | 24 w + 5 d | 28 w + 0 d | Yes |
| 0.30 | 2.76 | 809.1% | 25 w + 1 d | 27 w + 6 d | Yes |
| 0.12 | 1.15 | 830.9% | 20 w + 0 d | 27 w + 1 d | Yes |
| 0.08 | 0.96 | 1051.8% | 25 w + 6 d | 29 w + 6 d | Yes |
| 0.01 | 0.08 | 1200% | 21 w + 0 d | 27 w + 0 d | Yes |

TABLE 17

Categorized gain of sEng/PlGF ratio vs. final outcome

|  | PE/HELLP | [%] | No PE/HELLP | [%] |
|---|---|---|---|---|
| Gain <0% | 7 | 33.3 | 14 | 87.5 |
| Gain 0-100% | 3 | 14.3 | 0 | 0.0 |
| Gain 100-200% | 1 | 4.8 | 0 | 0.0 |
| Gain >200% | 10 | 47.6 | 2 | 12.5 |
| Sum | 21 | 100.0 | 16 | 100.0 |

Using 100%/200% of gain as cutoff, this can be transferred in terms of clinical sensitivity/specificity:

TABLE 18

Sens/Spec depending on gain as cutoff

| Cutoff at 100% | Sensitivity | 52.4% |
|---|---|---|
|  | Specificity | 87.5% |
| Cutoff at 200% | Sensitivity | 47.6% |
|  | Specificity | 87.% |

Figure 5A:
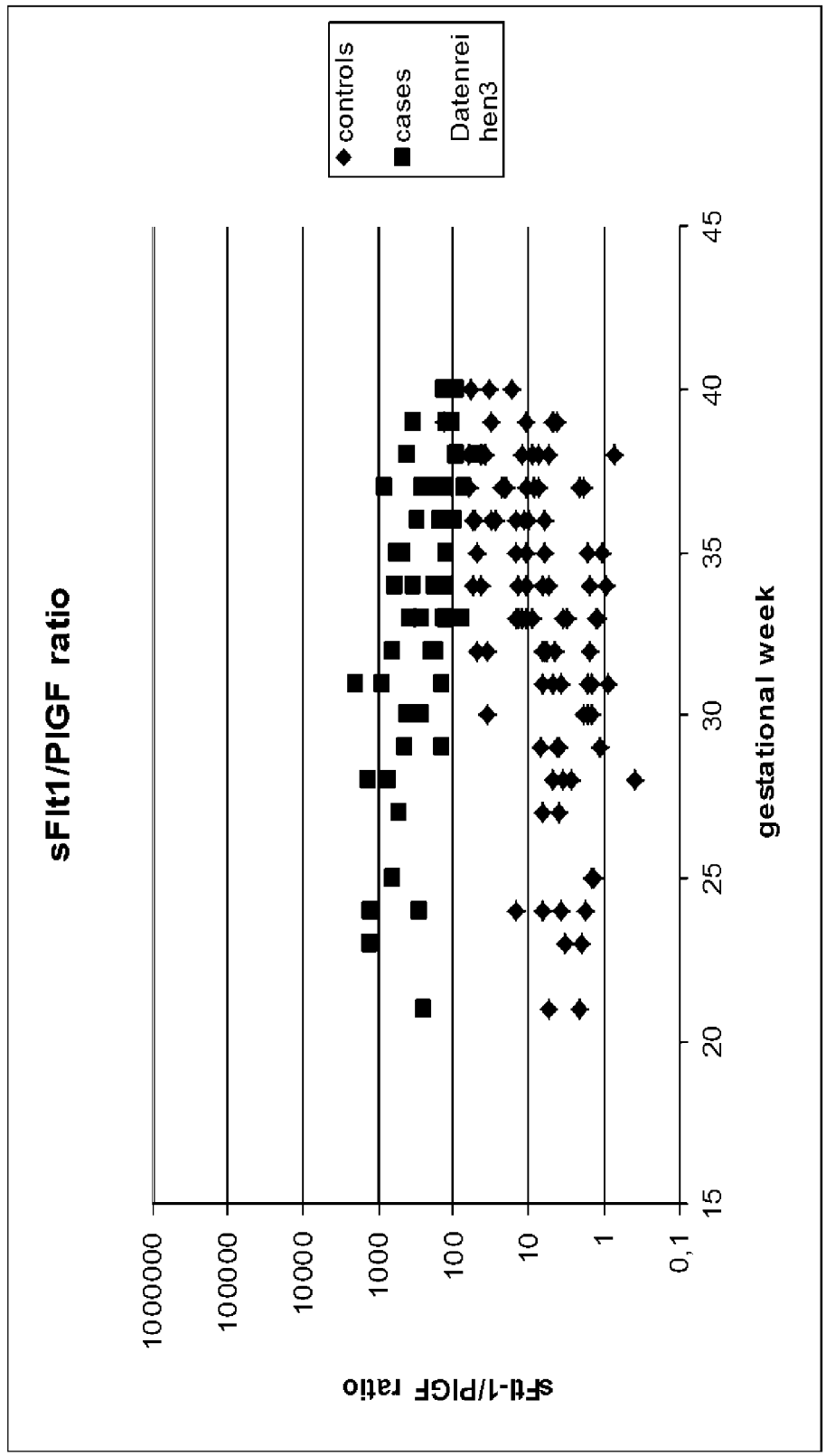
FIG. 5A shows sFlt-1/PlGF ratios at different weeks of gestation.
Figure 5B:
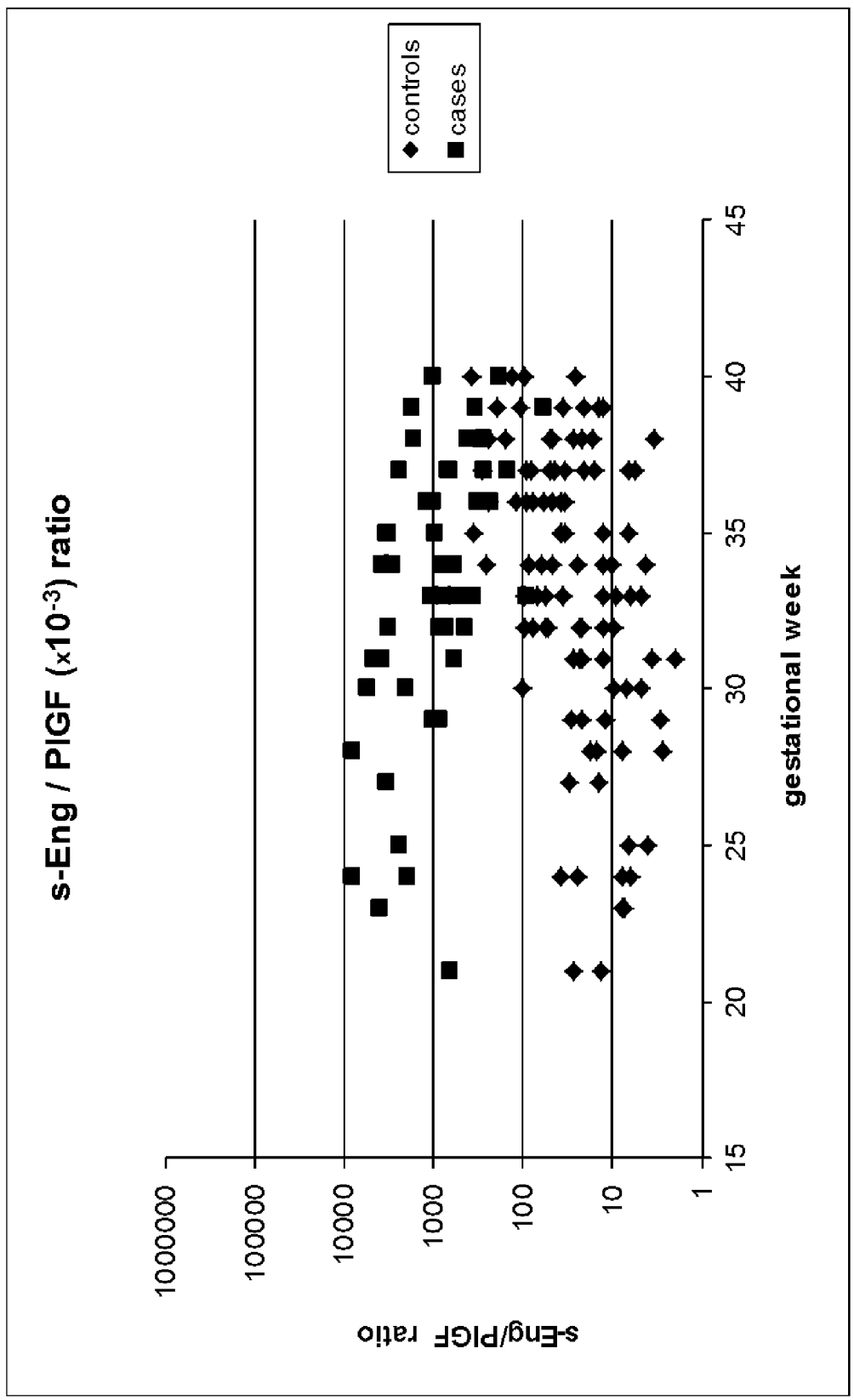
FIG. 5B shows Endoglin (sEng)/PlGF ratios at different weeks of gestation.
Figure 6A:
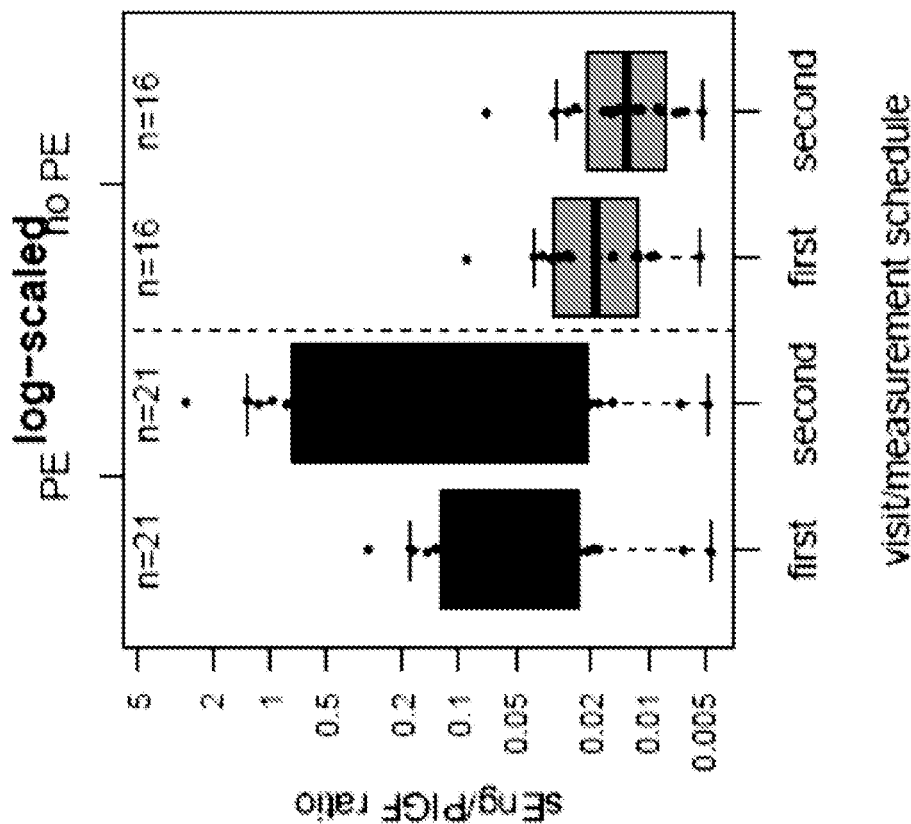
FIG. 6A shows sEng/PlGF ratios for the PE group and the healthy controls at different visits in normal scales.
Figure 6B:
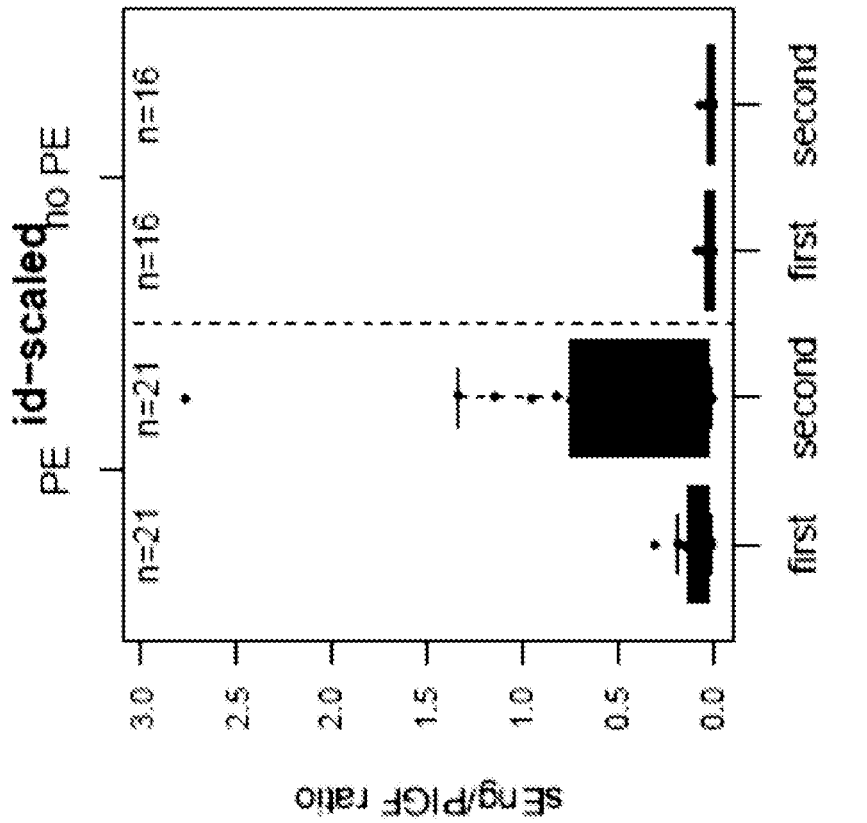
FIG. 6B shows sEng/PlGF ratios for the PE group and the healthy controls at different visits in log scales.
Figure 7B:
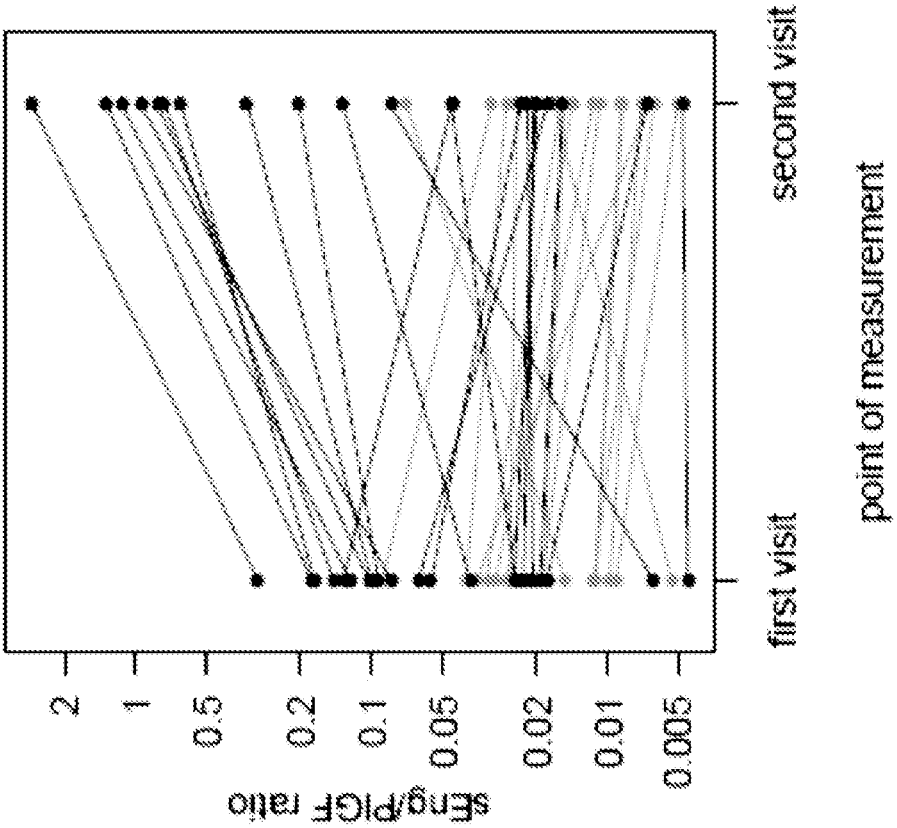
FIG. 7B shows differences of sEng/PlGF ratios compared to the time point of measurement.
Figure 7A:
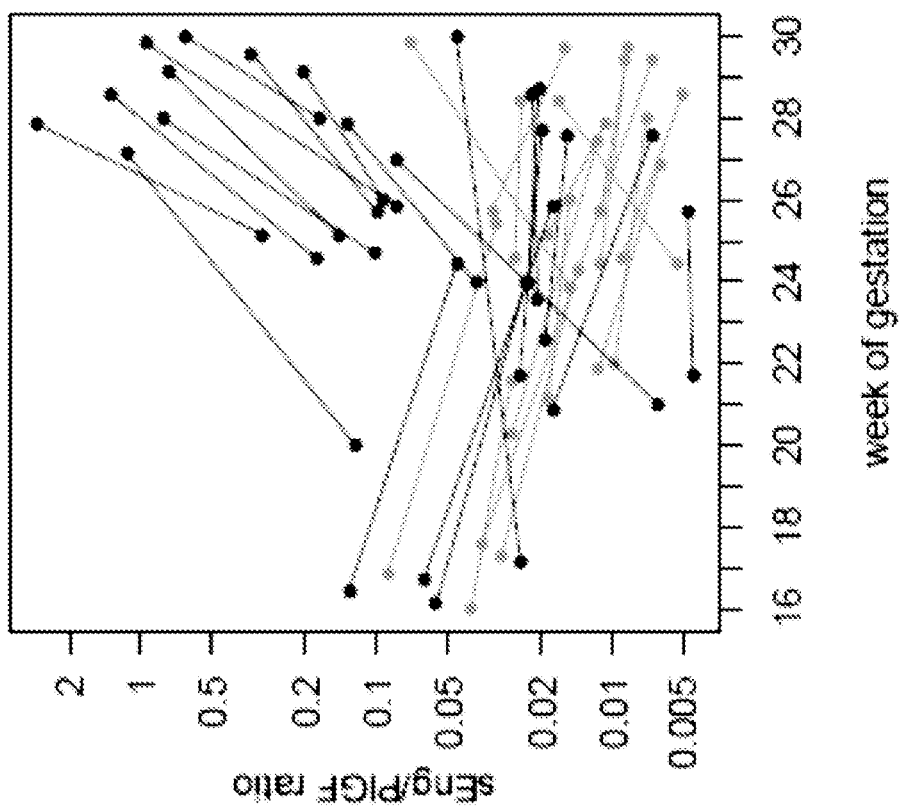
FIG. 7A shows differences of sEng/PlGF ratios compared to gestational age.
Figure 8A:
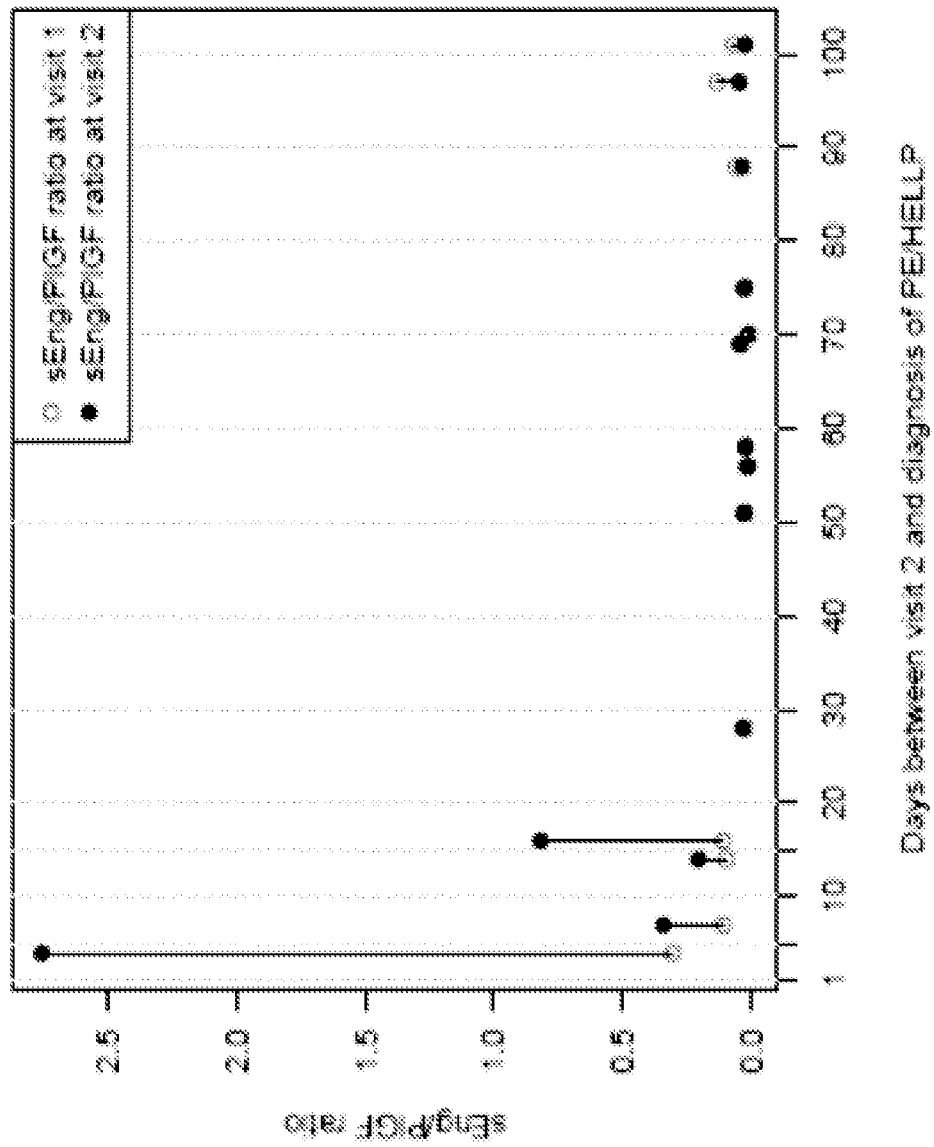
FIG. 8A shows a time to diagnosis of PE/HELLP versus values of sEng/PlGF ratio plot.
Figure 8B:
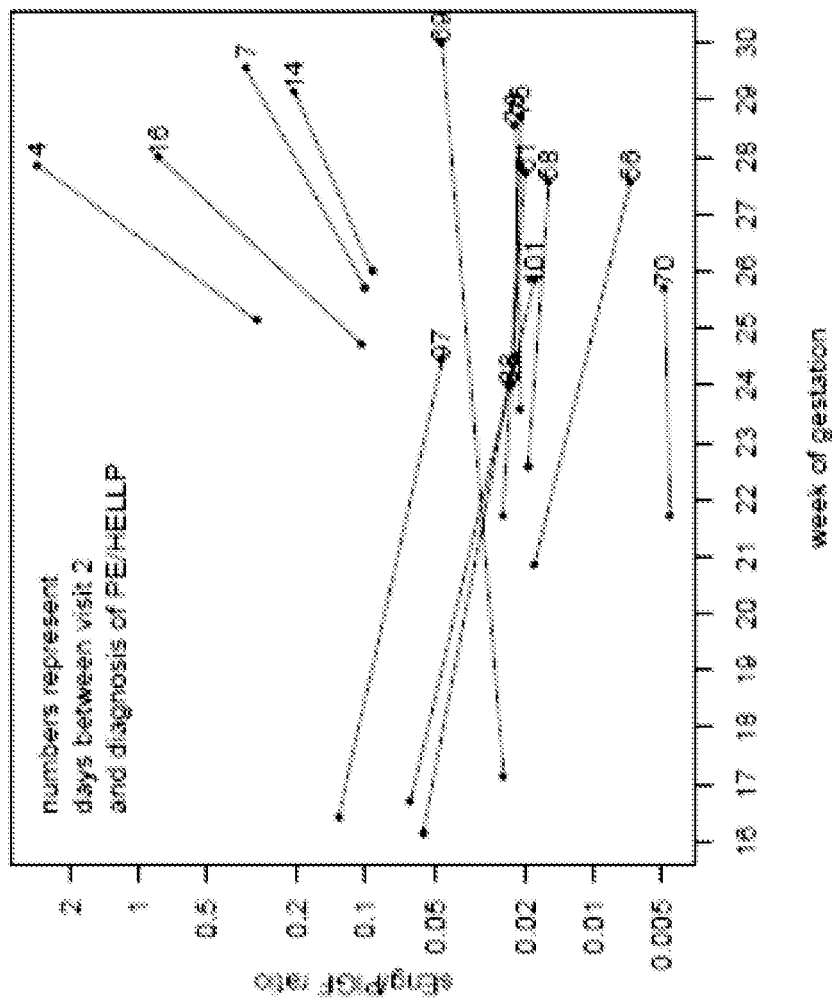
FIG. 8B shows the slopes between the sEng/PlGF ratios at first and second visit from patients of the PE/HELLP group.

The different ratios determined for sFlt-1 and PlGF at different time points of gestation for patients with preeclampsia and healthy controls are also indicated graphically in FIG. 5A. The same graph has been shown for the Endoglin/PlGF ratios; FIG. 5B. It is apparent that the ratios of sFlt-1/PlGF and Endoglin/PlGF show a similar distribution and, thus, are similar predictors for the development of preeclampsia.

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method for diagnosing and treating a pregnant subject being at risk of developing early onset preeclampsia comprising:
    a) measuring amounts of a first biomarker selected from the group consisting of soluble fms-like tyrosine kinase-1 (sFlt-1) and Endoglin and a second biomarker being placental growth factor (PlGF) in a first and a second sample of said subject, wherein said first sample has been obtained less than 4 weeks prior to said second sample, the second sample is obtained no later than week 30 of gestation, and wherein said first and second sample are independently selected from the group consisting of a blood sample, a serum sample and a plasma sample;
    b) determining a first ratio from said amounts of sFlt-1 to PlGF or Endoglin to PlGF measured in the first sample and a second ratio from said amounts of sFlt-1 to PlGF or Endoglin to PlGF determined in the second sample;
    c) diagnosing the subject as being at risk for developing early onset preeclampsia if the value of the second ratio is at least 3 times the value of the first ratio; and
    d) providing at least one supportive measure to a subject diagnosed as being at risk for developing preeclampsia within about 16 days,
wherein at least one supportive measure is administration of blood pressure reducing agents.

2. The method of claim 1, wherein said pregnant subject is between about week 15 and no later than week 30 of gestation.

3. The method of claim 1, wherein the amounts of first biomarker are measured by:
    contacting a portion of the first sample obtained from said subject with an antibody having specific binding affinity for sFlt-1 or Endoglin, thereby forming a complex between the antibody and sFlt-1 or Endoglin,
    wherein the antibody having specific bind affinity for sFl-1 comprises two monoclonal antibodies, wherein the first monoclonal antibody is biotinylated, and
    wherein the antibody having specific binding affinity for Endoglin is a monoclonal antibody;
    separating the complex formed in said step of contacting from antibody not comprising the complex; and
    quantifying a signal from the complex, the signal being proportional to the concentration of sFlt-1 or Endoglin in the sample obtained from the subject.

4. The method of claim 1, wherein the amounts of the second biomarker are measured as follows:
    contacting a portion of the first sample and the second sample obtained from said subject with an antibody having specific binding affinity for PlGF, thereby forming a complex between the antibody and PlGF;
    separating the complex formed in said step of contacting from antibody not comprising the complex; and quantifying a signal form the complex, the signal being proportional to the concentration of PIGF in the sample obtained from the subject.

\* \* \* \* \*